(12) United States Patent
Hofmann et al.

(10) Patent No.: US 10,359,398 B2
(45) Date of Patent: Jul. 23, 2019

(54) METHOD FOR DETERMINING CARBOHYDRATES STRUCTURE

(71) Applicants: Max-Planck-Gesellschaft zur Forderung der Wissenschaften e.V., Munich (DE); Freie Universitat Berlin, Berlin (DE)

(72) Inventors: Johanna Hofmann, Berlin (DE); Heung Sik Hahm, Charlottesville, VA (US); Peter Seeberger, Kleinmachnow (DE); Kevin Pagel, Berlin (DE)

(73) Assignees: Max-Planck-Gesellschaft zur Forderung der Wissenschaften e.V., Munich (DE); Freie Universitat Berlin, Berlin (DE)

( * ) Notice: Subject to any disclaimer, the term of this patent is extended or adjusted under 35 U.S.C. 154(b) by 0 days.

(21) Appl. No.: 15/757,019

(22) PCT Filed: Sep. 3, 2015

(86) PCT No.: PCT/EP2015/070195
§ 371 (c)(1),
(2) Date: Mar. 2, 2018

(87) PCT Pub. No.: WO2017/036545
PCT Pub. Date: Mar. 9, 2017

(65) Prior Publication Data
US 2018/0246062 A1    Aug. 30, 2018

(51) Int. Cl.
*G01N 27/62* (2006.01)
*G06F 19/16* (2011.01)
*G16B 15/00* (2019.01)
*G01N 33/68* (2006.01)

(52) U.S. Cl.
CPC ....... *G01N 27/622* (2013.01); *G01N 33/6848* (2013.01); *G16B 15/00* (2019.02); *G01N 2400/00* (2013.01); *G01N 2560/00* (2013.01)

(58) Field of Classification Search
CPC ............. G01N 27/622; G01N 33/6848; G01N 2400/00; G01N 2560/00; G06F 19/16
USPC ................................ 250/281, 282, 283, 288
See application file for complete search history.

(56) References Cited

PUBLICATIONS

Paglia et al. "Ion Mobility Derived Cross Sections to Support Metabolomics Application", Analytical Chemistry, vol. 88, Mar. 18, 2014, pp. 3985-3993.*

(Continued)

*Primary Examiner* — Nicole M Ippolito
(74) *Attorney, Agent, or Firm* — Amin, Turocy & Watson LLP

(57) ABSTRACT

The present invention relates to a method for determining in an expedient manner and with minimal sample consumption the structure of an unknown carbohydrate by using ion mobility-mass spectrometry (IM-MS) in negative ionization mode and fragmentation and a database containing structures of carbohydrates and/or of the fragments of the negative ions of carbohydrates, and for each of the structures of the target carbohydrates the collision cross section value and the mass-to-charge ratio value of the negative ion thereof, and for each of the structures of the fragments of the negative ions of the target carbohydrates the collision cross section value and the mass-to-charge ratio value of the fragment of the negative ion of the target carbohydrate.

15 Claims, 9 Drawing Sheets

I - Composition
Type of monosaccharide building block, e.g.

β-D-Glucose (Glc)

or

β-D-Galactose (Gal)

II - Connectivity
Position of glycosidic bond, e.g.

β-Gal-(1→3)-Gal or

β-Gal-(1→4)-Gal

III - Configuration
Stereochemistry of glycosidic bond, e.g.

β-Gal-(1→3)-Gal or

α-Gal-(1→3)-Gal

(56) References Cited

PUBLICATIONS

Paglia et al., "Ion Mobility Derived Collision Cross Sections to Support Metabolomics Applications" Anaytical Chemistry, Mar. 18, 2014, vol. 86, No. 8, pp. 3985-3993.

Paglia et al., "Ion Mobility-derived Collision Cross-Sections of Common Metabolites to Support Metabolomics Applications", Supporting Information, 22 pages.

Fenn et al., "Structural resolution of carbohydrate positional and structural isomers based on gas-phase ion mobility-mass spectrometry", Physical Chemistry Chemical Physics, 2011, vol. 13, No. 6, pp. 2196-2205.

Hofmann et al., "Estimating Collision Cross Sections of Negatively Charged N-Glycans using Traveling Wave Ion Mobility-Mass Spectrometry", Anaytical Chemistry, 2014, vol. 86, 10789-10795.

Struwe et al., "GlycoMob: an ion mobility-mass spectrometry collision cross section database for glycomics", Aug. 28, 2015, 6 pages.

Lanucara et al., "The power of ion mobility-mass spectrometry for structural characterization and the study of conformational dynamics", Nature Chemistry, vol. 6, Apr. 2014, pp. 281-294.

International Search Report for International Patent Application No. PCT/EP2015/070195 dated Oct. 9, 2015, 5 pages.

Written Opinion for International Patent Application No. PCT/EP2015/070195 dated Oct. 9, 2015, 7 pages.

\* cited by examiner

Figure 1
| I - Composition | II - Connectivity | III - Configuration |
|---|---|---|
| Type of monosaccharide building block, e.g. | Position of glycosidic bond, e.g. | Stereochemistry of glycosidic bond, e.g. |
| 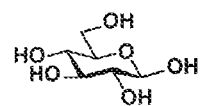<br>β-D-Glucose (Glc) | 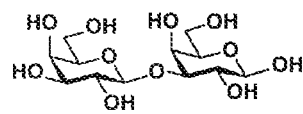<br>β-Gal-(1→3)-Gal | 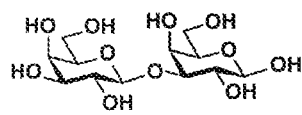<br>β-Gal-(1→3)-Gal |
| or | or | or |
| 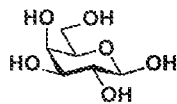<br>β-D-Galactose (Gal) | 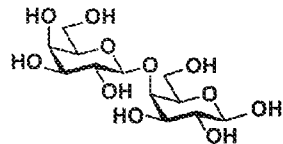<br>β-Gal-(1→4)-Gal | 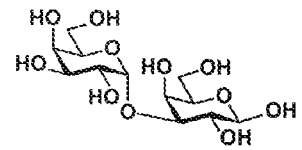<br>α-Gal-(1→3)-Gal |

METHOD FOR DETERMINING CARBOHYDRATES STRUCTURE

The present invention relates to a method for determining in an expedient manner and with minimal sample consumption the structure of an unknown carbohydrate by using ion mobility-mass spectrometry (IM-MS) in negative ionization mode and fragmentation and a database containing structures of carbohydrates and/or of the fragments of the negative ions of carbohydrates, and for each of the structures of the target carbohydrates the collision cross section value and the mass-to-charge ratio value of the negative ion thereof, and for each of the structures of the fragments of the negative ions of the target carbohydrates the collision cross section value and the mass-to-charge ratio value of the fragment of the negative ion of the target carbohydrate.

BACKGROUND OF THE INVENTION

The inherent structural diversity of carbohydrates poses a major analytical challenge to all aspects of the glycoscience and is one reason why glycomics lags behind the advances that have been made in genomics and proteomics. The structure of a carbohydrate is described by its composition, connectivity, and configuration (see FIG. 1). The carbohydrates or glycans are composed essentially of monosaccharides (e.g. D-heptoses, L-heptoses, D-hexoses, L-hexoses, D-pentoses, L-pentoses, D-tetroses, L-tetroses, sialic acids), which are connected to each other via glycosidic linkages (e.g. $\alpha$-(1→2), $\beta$-(1→2), $\alpha$-(1→3), $\beta$-(1→3), $\alpha$-(1→4), $\beta$-(1→4), $\alpha$-(1→5), $\beta$-(1→5), $\alpha$-(1→6), $\beta$-(1→6)). The composition of a carbohydrate (I) is defined by the monosaccharides (e.g. Glc, Man, Gal, Fuc) that are forming said carbohydrate. These building blocks are often stereoisomers that differ merely in the stereochemistry at one particular carbon atom, as in the case of glucose (Glc) and galactose (Gal). Each monosaccharide contains multiple hydroxyl groups that can be a point of attachment for a glycosidic linkage with the next monosaccharide. Thus, unlike oligonucleotides and proteins, carbohydrates are not necessarily linear, but rather can be branched structures with diverse regiochemistry (II). Additionally, a new stereocenter emerges when a glycosidic bond is formed, because two monosaccharides can be connected in two different configurations (III), thus leading to $\alpha$ and $\beta$ anomers.

Carbohydrates structure is typically ascertained by a combination of nuclear magnetic resonance spectroscopy (NMR) and mass spectrometry (MS). Measuring a mass-to-charge ratio (m/z) with MS is fast, requires very little sample and provides precise, high-resolution data about the sample composition. Detailed information regarding connectivity can be obtained following derivatisation and/or elaborate tandem MS analysis. Nevertheless, with MS it is not possible to analyze stereoisomers, since they generally cannot be distinguished due to their identical atomic composition and mass.

NMR experiments serve best to determine configurational information of carbohydrates, but require large amounts of sample, are time consuming and the resulting spectra are cumbersome to interpret when different stereoisomers need to be distinguished. In addition, the relative detection limit of 3-5% for larger oligosaccharides in NMR experiments is rather poor. Liquid chromatography (LC) can help to differentiate configurational isomers, but an unambiguous identification of one isomer in the presence of another is often not possible either.

To overcome the above-mentioned limitations, it is the objective of the present invention to provide a method for determining in an expedient manner and with minimal sample consumption the structure of a target carbohydrate by using ion mobility-mass spectrometry (IM-MS) in negative ionization mode. Herein, the negative ions of the carbohydrates, as well as the fragments of the negative ions of the carbohydrates are not only separated according to their mass and charge, but also based on their size and shape, thereby providing information about the underlying three-dimensional structure. IM-MS measures the drift time i.e. the time that ions require to drift through a cell that is filled with an inert neutral gas, such as helium or nitrogen, under the influence of a weak electric field. During this, compact ions undergo fewer collisions with the gas than more extended ions, and therefore traverse the cell faster. The measured drift time can be converted into an instrument-independent, rotationally averaged collision cross section (CCS) by methods known to the skilled person in the art (*Anal. Chem.* 2013, 85, 5138-5145; *Anal. Chem.* 2014, 86, 10789-10795). The rotationally-averaged collision cross-section (CCS) represents the effective area for the interaction between an individual ion and the neutral gas through which it is travelling. The CCS is intrinsic to a particular carbohydrate and is influenced by both the ionic state (i.e. positive/negative mode and adduction), as well as the particular drift gas.

The objective of the present invention is solved by the teaching of the independent claims. Further advantageous features, aspects and details of the invention are evident from the dependent claims, the description, the figures, and the examples of the present application.

DESCRIPTION OF THE INVENTION

In the present invention, it was found that the structure of an unknown carbohydrate, including the compositional structure (i.e. the monosaccharide(s) composing the unknown carbohydrate), the connectivity between the monosaccharides composing the unknown carbohydrate and the stereochemistry of each of the anomeric carbons of the unknown carbohydrate, can be determined in an expedient manner and with minimal sample consumption by using ion mobility-mass spectrometry in negative ionization mode and optionally fragmentation, and a database comprising the structures of the target carbohydrates and/or of the fragments of the negative ions of the target carbohydrates, and for each of the structures of the target carbohydrates the collision cross section value and the mass-to-charge ratio value of the negative ion thereof, and for each of the structures of the fragments of the negative ions of the target carbohydrates the collision cross section value and the mass-to-charge ratio value of the fragment of the negative ion of the target carbohydrate (see FIG. 3). The method described herein enables also the determination of the structure of each of the target carbohydrates present in a sample containing several target carbohydrates, as well as the structure (see FIG. 6) and optionally the relative concentration ratio of each of the several isobaric target carbohydrates present in a sample containing several isobaric carbohydrates (see FIG. 8).

Thus, the present invention is directed to a method for determining the structure of a target carbohydrate by ion mobility-mass spectrometry in negative ionization mode comprising the steps:

A) providing a sample containing the target carbohydrate; and

B) providing a database comprising the structures of the target carbohydrates and/or of the fragments of the negative ions of the target carbohydrates and for each of the structures of the target carbohydrates the collision cross section value and the mass-to-charge ratio value of the negative ion thereof, and for each of the structures of the fragments of the negative ions of the target carbohydrates the collision cross section value and the mass-to-charge ratio value of the fragment of the negative ion of the target carbohydrate; and C) measuring the drift time value and the mass-to-charge ratio value of a negative ion of the target carbohydrate; and D) converting the drift time value measured at step C) to the corresponding collision cross section value; and E) comparing the collision cross section value determined at step D) and the mass-to-charge ratio value measured at step C) with the cross section values and mass-to-charge ratio values stored in the database; and F) determining the structure of the target carbohydrate.

Preferably, the method according to the present invention further comprises steps E1), E2), E3) and E4) performed after step E) and before step F):

E1) subjecting a negative ion of the target carbohydrate to fragmentation to generate fragments of the negative ion of the target carbohydrate;

E2) measuring the drift time values and the mass-to-charge ratio values of the fragments of the negative ion of the target carbohydrate, which were generated at step E1);

E3) converting the drift time values measured at step E2) to the corresponding collision cross section values; and E4) comparing the collision cross section values determined at step E3) and the mass-to-charge ratio values measured at step E2) of the fragments of the negative ion of the target carbohydrate with cross section values and mass-to-charge ratio values stored in the database.

Hence, herein claimed is a method for determining the structure of a target carbohydrate by ion mobility-mass spectrometry in negative ionization mode and fragmentation comprising the steps:

A) providing a sample containing the target carbohydrate; and

B) providing a database comprising the structures of the target carbohydrates and/or of the fragments of the negative ions of the target carbohydrates and for each of the structures of the target carbohydrates the collision cross section value and the mass-to-charge ratio value of the negative ion thereof, and for each of the structures of the fragments of the negative ions of the target carbohydrates the collision cross section value and the mass-to-charge ratio value of the fragment of the negative ion of the target carbohydrate; and C) measuring the drift time value and the mass-to-charge ratio value of a negative ion of the target carbohydrate; and D) converting the drift time value measured at step C) to the corresponding collision cross section value; and E) comparing the collision cross section value determined at step D) and the mass-to-charge ratio value measured at step C) with the cross section values and mass-to-charge ratio values stored in the database; and E1) subjecting a negative ion of the target carbohydrate to fragmentation to generate fragments of the negative ion of the target carbohydrate; and E2) measuring the drift time values and the mass-to-charge ratio values of the fragments of the negative ion of the target carbohydrate, which were generated at step E1); and E3) converting the drift time values measured at step E2) to the corresponding collision cross section values; and E4) comparing the collision cross section values determined at step E3) and the mass-to-charge ratio values measured at step E2) of the fragments of the negative ion of the target carbohydrate with cross section values and mass-to-charge ratio values stored in the database; and F) determining the structure of the target carbohydrate.

Alternatively, steps E1), E2), E3) and E4) are performed after step D) and before step F). Thus, herein claimed is a method for determining the structure of a target carbohydrate by ion mobility-mass spectrometry in negative ionization mode and fragmentation comprising the steps:

A), B), C), D), E1), E2), E3), E4), E) and F); or

A), B), C), D), E), E1), E2), E3), E4) and F), wherein steps A), B), C), D), E1), E2), E3), E4), E) and F) have the meanings defined herein.

Preferably, steps E4) and E) are performed simultaneously. Hence, herein claimed is also a method for determining the structure of a target carbohydrate by ion mobility-mass spectrometry in negative ionization mode and fragmentation comprising the steps:

A) providing a sample containing the target carbohydrate; and

B) providing a database comprising the structures of the target carbohydrates and/or of the fragments of the negative ions of the target carbohydrates and for each of the structures of the target carbohydrates the collision cross section value and the mass-to-charge ratio value of the negative ion thereof, and for each of the structures of the fragments of the negative ions of the target carbohydrates the collision cross section value and the mass-to-charge ratio value of the fragment of the negative ion of the target carbohydrate; and C) measuring the drift time value and the mass-to-charge ratio value of a negative ion of the target carbohydrate; and D) converting the drift time value measured at step C) to the corresponding collision cross section value; and E1) subjecting a negative ion of the target carbohydrate to fragmentation to generate fragments of the negative ion of the target carbohydrate; and E2) measuring the drift time values and the mass-to-charge ratio values of the fragments of the negative ion of the target carbohydrate, which were generated at step E1); and E3) converting the drift time values measured at step E2) to the corresponding collision cross section values; and E5) comparing the collision cross section value determined at step D) and the mass-to-charge ratio value measured at step C) and the collision cross section values determined at step E3) and the mass-to-charge ratio values measured at step E2) of the fragments of the negative ion of the target carbohydrate with cross section values and mass-to-charge ratio values stored in the database; and F) determining the structure of the target carbohydrate.

Surprisingly, it was found that fragmentation of a negative ion of a target carbohydrate generates fragments exhibiting an identical CCS with their intact carbohydrate counterparts. This finding is illustrated by FIG. 4, which clearly shows that subjecting the deprotonated pentasaccharide 7 to fragmentation leads to fragments, such as the trisaccharide fragment, of identical mass and CCS with the deprotonated trisaccharide 6. Hence, based on the information stored in the database, the structure of large carbohydrates including the compositional structure, the connectivity between the monosaccharides composing the unknown carbohydrate and the stereochemistry of each of the anomeric carbons, can be determined by using the method described herein. Moreover, FIG. 5 demonstrates the importance of the fragmentation for the differentiation and assignment of structures to large carbohydrates.

As used herein the term "target carbohydrate" or "unknown carbohydrate" refers to a synthetic carbohydrate, a semi-synthetic carbohydrate or a carbohydrate isolated from natural sources, whose structure needs to be determined or assigned. The target carbohydrate comprises preferably between 1 and 50 monosaccharides, more preferably between 2 and 25 monosaccharides, and still more preferably between 3 and 10 monosaccharides. The monosaccharides preferably from belong to heptoses, hexoses, pentoses, tetroses or sialic acids. The monosaccharides are preferably connected through glycosidic linkages selected from: α-(1→2), β-(1→2), α-(1→3), β-(1→3), α-(1→4), β-(1→4), α-(1→5), β-(1→5), α-(1→6), β-(1→6), α-(2→2), β-(2→2), α-(2→3), β-(2→3), α-(2→4), β-(2→4), α-(2→5), β-(2→5), α-(2→6), β-(2→6), α-(2→8), and β-(2→8).

Preferably, the monosaccharides forming the target carbohydrate are selected from: α-D-Glcp, β-D-Glcp, α-L-Glcp, β-L-Glcp, α-D-Glcf, β-D-Glcf, α-L-Glcf, β-L-Glcf, α-D-Galp, β-D-Galp, α-L-Galp, β-L-Galp, α-D-Galf, β-D-Galf, α-L-Galf, β-L-Galf, α-D-Manp, β-D-Manp, α-L-Manp, β-L-Manp, α-D-Manf, β-D-Manf, α-L-Manf, β-L-Manf, α-D-Allp, β-D-Allp, α-L-Allp, β-L-Allp, α-D-Allf, β-D-Allf, α-L-Allf, β-L-Allf, α-D-Altp, β-D-Altp, α-L-Altp, β-L-Altp, α-D-Altf, β-D-Altf, α-L-Altf, β-L-Altf, α-D-Gulp, β-D-Gulp, α-L-Gulp, β-L-Gulp, α-D-Gulf, β-D-Gulf, α-L-Gulf, β-L-Gulf, α-D-Idop, β-D-Idop, α-L-Idop, β-L-Idop, α-D-Idof, β-D-Idof, α-L-Idof, β-L-Idof, α-D-Talp, β-D-Talp, α-L-Talp, β-L-Talp, α-D-Talf, β-D-Talf, α-L-Talf, β-L-Talf, α-D-Ribp, β-D-Ribp, α-L-Ribp, β-L-Ribp, α-D-Ribf, β-D-Ribf, α-L-Ribf, β-L-Ribf, α-D-Arap, β-D-Arap, α-L-Arap, β-L-Arap, α-D-Araf, β-D-Araf, α-L-Araf, β-L-Araf, α-D-Xylp, β-D-Xylp, α-L-Xylp, β-L-Xylp, α-D-Xylf, β-D-Xylf, α-L-Xylf, β-L-Xylf, α-D-Lyxp, β-D-Lyxp, α-L-Lyxp, β-L-Lyxp, α-D-Lyxf, β-D-Lyxf, α-L-Lyxf, β-L-Lyxf, α-D-Eryf, β-D-Eryf, α-L-Eryf, β-L-Eryf, α-D-Thof, β-D-Thof, α-L-Thof, β-L-Thof, α-D-GlcAp, β-D-GlcAp, α-L-GlcAp, β-L-GlcAp, α-D-GlcAf, β-D-GlcAf, α-L-GlcAf, β-L-GlcAf, α-D-GlcNp, β-D-GlcNp, α-L-GlcNp, β-L-GlcNp, α-D-GlcNf, β-D-GlcNf, α-L-GlcNf, β-L-GlcNf, α-D-GlcNAcp, β-D-GlcNAcp, α-L-GlcNAcp, β-L-GlcNAcp, α-D-GlcNAcf, β-D-GlcNAcf, α-L-GlcNAcf, β-L-GlcNAcf, α-D-GalAp, β-D-GalAp, α-L-GalAp, β-L-GalAp, α-D-GalAf, β-D-GalAf, α-L-GalAf, β-L-GalAf, α-D-GalNp, β-D-GalNp, α-L-GalNp, β-L-GalNp, α-D-GalNf, β-D-GalNf, α-L-GalNf, β-L-GalNf, α-D-GalNAcp, β-D-GalNAcp, α-L-GalNAcp, β-L-GalNAcp, α-D-GalNAcf, β-D-GalNAcf, α-L-GalNAcf, β-L-GalNAcf, α-D-ManAp, β-D-ManAp, α-L-ManAp, β-L-ManAp, α-D-ManAf, β-D-ManAf, α-L-ManAf, β-L-ManAf, α-D-ManNp, β-D-ManNp, α-L-ManNp, β-L-ManNp, α-D-ManNf, β-D-ManNf, α-L-ManNf, β-L-ManNf, α-D-ManNAcp, β-D-ManNAcp, α-L-ManNAcp, β-L-ManNAcp, α-D-ManNAcf, β-D-ManNAcf, α-L-ManNAcf, β-L-ManNAcf, α-D-Fucp, β-D-Fucp, α-L-Fucp, β-L-Fucp, α-D-Fucf, β-D-Fucf, α-L-Fucf, β-L-Fucf, α-D-FucNp, β-D-FucNp, α-L-FucNp, β-L-FucNp, α-D-FucNf, β-D-FucNf, α-L-FucNf, β-L-FucNf, α-D-FucNAcp, β-D-FucNAcp, α-L-FucNAcp, β-L-FucNAcp, α-D-FucNAcf, β-D-FucNAcf, α-L-FucNAcf, β-L-FucNAcf, α-D-Rhap, β-D-Rhap, α-L-Rhap, β-L-Rhap, α-D-Rhaf, β-D-Rhaf, α-L-Rhaf, β-L-Rhaf, α-D-Quip, β-D-Quip, α-L-Quip, β-L-Quip, α-D-Quif, β-D-Quif, α-L-Quif, β-L-Quif, α-D-QuiNp, β-D-QuiNp, α-L-QuiNp, β-L-QuiNp, α-D-QuiNf, β-D-QuiNf, α-L-QuiNf, β-L-QuiNf, α-D-QuiNAcp, β-D-QuiNAcp, α-L-QuiNAcp, β-L-QuiNAcp, α-D-QuiNAcf, β-D-QuiNAcf, α-L-QuiNAcf, β-L-QuiNAcf, α-D-IdoAp, β-D-IdoAp, α-L-IdoAp, β-L-IdoAp, α-D-IdoAf, β-D-IdoAf, α-L-IdoAf, β-L-IdoAf, α-Sia, β-Sia, α-Neu, β-Neu, α-Neu5Ac, β-Neu5Ac, Ery-ol, Ara-ol, Xyl-ol, Rib-ol, Glc-ol, Gal-ol, Man-ol, α-D-Psip, β-D-Psip, α-L-Psip, β-L-Psip, α-D-Psif, β-D-Psif, α-L-Psif, β-L-Psif, α-D-Frup, β-D-Frup, α-L-Frup, β-L-Frup, α-D-Fruf, β-D-Fruf, α-L-Fruf, β-L-Fruf, α-D-Xulf, β-D-Xulf, α-L-Xulf, β-L-Xulf, α-D-Sorp, β-D-Sorp, α-L-Sorp, β-L-Sorp, α-D-Sorf, β-D-Sorf, α-L-Sorf, β-L-Sorf, α-D-Tagp, β-D-Tagp, α-L-Tagp, β-L-Tagp, α-D-Tagf, β-D-Tag f, α-L-Tagf, β-L-Tagf, Kdo, Kdn (Glc=glucose; Gal=galactose; Man=mannose; All=allose; Alt=altrose; Gul=gulose; Ido=idose; Tal=talose; Rib=ribose; Ara=arabinose; Xyl=xylose; Lyx=lyxose; Ery=erythrose; Tho=threose; GlcA=glucuronic acid; GlcN=2-amino-2-deoxyglucose; GlcNAc=2-acetamido-2-deoxyglucose; GalA=galacturonic acid; GalN=2-amino-2-deoxygalactose; GalNAc=2-acetamido-2deoxygalactose;

ManA=mannuronic acid; ManN=2-amino-2-deoxy-mannose; ManNAc=2-acetamido-2-deoxy-mannose; Fuc=fucose; FucN=2-amino-2-deoxyfucose; FucNAc=2-acetamido-2-deoxy-fucose; Rha=rhamnose; Qui=quinovose; QuiN=2-amino-2-deoxy-quinovose; QuiNAc=2-acetamido-2-deoxy-quinovose; IdoA=iduronic acid; Sia=sialic acid; Neu=neuraminic acid; Neu5Ac=N-acetyl-neuraminic acid; Ery-ol=erythritol; Ara-ol=arabinitol, Xyl-ol=xylitol; Rib-ol=ribitol; Glc-ol=glucitol; Gal-ol=galactitol; Man-ol=mannitol; Psi=psicose; Fru=fructose; Xul=xylulose; Sor=sorbose; Tag=tagatose; Kdo=3-deoxy-D-manno-oct-2-ulosonic acid; Kdn=3-deoxy-D-glycero-D-galacto-non-2-ulosonic acid)

It is preferred that the target carbohydrate is a synthetic carbohydrate further comprising a linker covalently bound to the anomeric carbon of the reducing end monosaccharide of the synthetic carbohydrate. Examples of such linkers are well known to the person skilled in the art and include, but are not restricted to: $-O-(CH_2)_m-CH_3$, $-O-(CH_2)_n-NH_2$, $-O-(CH_2)_n-SH$, $-O-(CH_2-CH_2-O)_o-C_2H_4-NH_2$, $-O-(CH_2-CH_2-O)_o-C_2H_4-NH_2$, wherein m is an integer selected from 0, 1, 2, 3, 4, 5, 6, 7, 8, 9 and 10; n is an integer selected from 1, 2, 3, 4, 5, 6, 7, 8, 9 and 10; and o is an integer selected from 1, 2, 3, 4 and 5.

It is further preferred that the target carbohydrate is a carbohydrate isolated from natural sources. Examples of carbohydrates isolated from natural sources include, but are not restricted to O-glycans, N-glycans, milk sugars, bacterial oligosaccharides, bacterial polysaccharides. Methods for isolating carbohydrates from natural sources are well described in the literature (for the release and isolation of O-glycans and N-glycans see for e.g. *Biochemistry* 1993, 32, 679-693; *Biochemistry* 1985, 24, 4665-4671; for isolation of bacterial oligosaccharides and polysaccharides see for e.g. *Ohio Journal of Science* 1956, 1, 41-51).

As used herein the term "sample containing the target carbohydrate" or "sample comprising the target carbohydrate" encompasses a solution consisting of the analyte comprising the target carbohydrate i.e. the carbohydrate whose structure has to be determined in a solvent.

The analyte comprising the target carbohydrate can be the target carbohydrate with a purity of at least 99%, or a mixture of several target carbohydrates, such as isobaric carbohydrates. Isobaric carbohydrates are carbohydrates having an identical atomic composition and mass, but different structures. Isobaric carbohydrates are for example diastereoisomers including those differing only through the stereochemistry of one chiral center, such as anomers, and glycosidic linkage regioisomers, which differ in their connectivity and/or branching. Optionally, the analyte further comprises one or more impurities. Examples of impurities include, but are not restricted to peptides, glycopeptides, lipids, glycolipids and salts. Such impurities can be side-products generated during the synthetic process or impurities that could not be separated during the isolation process. If an analyte comprises several target carbohydrates, the structure of each of the target carbohydrates is determined. Moreover, the present method enables even the determination of the structure of each of the isobaric carbohydrates present in a mixture of isobaric carbohydrates (see FIG. 6). Additionally, the present method allows the determination of the relative concentration ratio of each of the several isobaric target carbohydrates present in the analyte (see FIG. 8).

The analyte used for the preparation of the sample provided at step A) can contain even less than 0.1% by weight of a target carbohydrate. In such a case, high intensity measurements of the drift time value and m/z value enables the detection of the target carbohydrate and the determination of its structure (see FIG. 2). Preferably, the analyte contains at least 25% by weight of a target carbohydrate, more preferably at least 50% by weight of a target carbohydrate and even more preferably at least 75% by weight of a target carbohydrate.

Preferably the solvent is selected from: water, methanol, chloroform, acetonitrile, isopropanol and mixtures thereof.

As used herein the wording "determining the structure of the target carbohydrate" includes:
  determining the compositional structure of the target carbohydrate i.e. all the monosaccharides and eventually the linker composing the target carbohydrate; and
  determining the linkage connectivity between the monosaccharides (for e.g. 1→2, 1→3, 1→4, 1→5, 1→6, 2→2, 2→3, 2→4, 2→5, 2→6, 2→8 etc.); and
  determining the stereochemistry of each of the anomeric carbons of the target carbohydrate.

As demonstrated for example by FIGS. 3, 7, 9, the method described herein enables even the differentiation of structurally closed target carbohydrates, such as diastereoisomers including those differing only through the stereochemistry of one chiral center, such as anomers, and glycosidic linkage regioisomers (for e.g. 1→2 versus 1→3 connection of the same monosaccharides).

As used herein the wording "providing a database comprising the structures of the target carbohydrates and/or of the fragments of the negative ions of the target carbohydrates, and for each of the structures of the target carbohydrates the collision cross section value and the mass-to-charge ratio value of the negative ion thereof, and for each of the structures of the fragments of the negative ions of the target carbohydrates the collision cross section value and the mass-to-charge ratio value of the fragment of the negative ion of the target carbohydrate" or "providing a database containing the structures of the target carbohydrates and/or of the fragments of the negative ions of the target carbohydrates and for each of the structures of the target carbohydrates the collision cross section value and the mass-to-charge ratio value of the negative ion thereof, and for each of the structures of the fragments of the negative ions of the target carbohydrates the collision cross section value and the mass-to-charge ratio value of the fragment of the negative ion of the target carbohydrate" refers to a database including a number of entries, each entry being specific to a carbohydrate or to fragment of a negative ion of a carbohydrate, wherein said number of entries enables the assignment of the structure to any unknown carbohydrate or any target carbohydrate or any carbohydrate whose structure needs to be determined using the inventive method described herein. Each entry of the database is specific to a carbohydrate or to a fragment of a negative ion of a carbohydrate and contains:
  the structure of the carbohydrate or the structure of a fragment of a negative ion of the carbohydrate; and
  the collision cross section value (CCS) and the mass-to-charge ratio value (m/z) of the negative ion of the target carbohydrate or of the fragment of a negative ion of the target carbohydrate "A fragment of a negative ion of the target carbohydrate" refers to a substructure of a negative ion of the target carbohydrate that was generated following fragmentation by collision induced dissociation (CID), electron-transfer dissociation (ETD) or electron-capture dissociation (ECD).

As used herein the wording "negative ion of the target carbohydrate" refers to the deprotonated ion of the target carbohydrate or the anion complex of the target carbohydrate with chloride ($Cl^-$), acetate ($CH_3CO_2^-$), monochloroacetate ($CH_2ClCO_2^-$), dichloroacetate ($CHCl_2CO_2^-$), trifluoroacetate ($CF_3CO_2^-$), formate ($HCO_2^-$), trichloroacetate ($CCl_3Co_2^-$), monobromoacetate ($CH_2BrCO_2^-$), dibromoacetate ($CHBr_2CO_2^-$), tribromoacetate ($CBr_3CO_2^-$), bromochloroacetate ($CBrClHCo_2^-$), chlorodibromoacetate ($CClBr_2CO_2^-$), bromodichloroacetate ($CBrCl_2CO_2^-$), nitrate ($NO_3^-$) or phosphate ($H_2PO_4^-$).

Each negative ion of a target carbohydrate and each fragment of a negative ion of the target carbohydrate is characterized by a collision cross section value (CCS) and a mass-to-charge ratio value (m/z). Using IM-MS in negative ionization mode, a drift time value and a mass-to-charge ratio value (m/z) can be measured for each negative ion. Using protocols known to the skilled person (*Anal. Chem.* 2013, 85, 5138-5145; *Anal. Chem.* 2014, 86, 10789-10795) the drift time value for said negative ion is converted to the collision cross section value (CCS) for a said negative ion. Depending on the inert drift gas (e.g., helium, nitrogen, argon or carbon dioxide) used during the measurement of the drift time value, several collision cross section values, each specific to a drift gas, can be determined for a given negative ion.

Table 1 illustrates an entry specific to a target carbohydrate into the database.

| Structure Target Carbohydrate | | | |
| --- | --- | --- | --- |
| Negative ion | $CCS_{He}$ (Å$^2$) | $CCS_{N2}$ (Å$^2$) | m/z |
| $[M - H]^-$ | | | |
| $[M + Cl]^-$ | | | |
| $[M + CH_3CO_2]^-$ | | | |
| $[M + CH_2ClCO_2]^-$ | | | |
| $[M + CHCl_2CO_2]^-$ | | | |
| $[M + CCl_3CO_2]^-$ | | | |
| $[M + CH_2BrCO_2]^-$ | | | |
| $[M + CHBr_2CO_2]^-$ | | | |
| $[M + CBr_3CO_2]^-$ | | | |
| $[M + CBrClHCO_2]^-$ | | | |
| $[M + CBrCl_2CO_2]^-$ | | | |
| $[M + H_2PO_4]^-$ | | | |

Preferably, the database of step B) of the inventive method contains or comprises at least entries for the following monosaccharides:

D-Glc, L-Glc, D-Gal, L-Gal, D-Man, L-Man, D-All, L-All, D-Alt, L-Alt, D-Gul, L-Gul, D-Ido, L-Ido, D-Tal, L-Tal, D-Rib, L-Rib, D-Ara, L-Ara, D-Xyl, L-Xyl, D-Lyx, L-Lyx, D-Ery, L-Ery, D-Tho, L-Tho, D-GlcA, L-GlcA, D-GlcN, L-GlcN, D-GlcNAc, L-GlcNAc, D-GalA, L-GalA, D-GalN, L-GalN, D-GalNAc, L-GalNAcp, D-ManA, L-ManA, D-ManN, L-ManN, D-ManNAc, L-ManNAc, D-Fuc, L-Fuc, D-FucN, L-FucN, D-FucNAc, L-FucNAc, D-Rha, L-Rhap, D-Qui, L-Quip, D-QuiN, L-QuiN, D-QuiNAc, L-QuiNAc, D-IdoA, L-IdoA, α-Sia, β-Sia, α-Neu, β-Neu, α-Neu5Ac, β-Neu5Ac, Ery-ol, Ara-ol, Xyl-ol, Rib-ol, Glc-ol, Gal-ol, Man-ol, D-Psi, L-Psi, D-Fru, L-Fru, D-Xul, L-Xul, D-Sor, L-Sor, D-Tag, L-Tag, Kdn, Kdo, α- and β-pyranosides and furanosides thereof presenting a linker bound at the anomeric carbon, disaccharides thereof presenting or not a linker bound at the anomeric carbon of the reducing end monosaccharide and trisaccharides thereof presenting or not a linker bound at the anomeric carbon of the reducing end monosaccharide.

More preferably, the database of step B) contains or comprises at least entries for the above-mentioned monosaccharides, α- and β-pyranosides and furanosides thereof presenting a linker bound at the anomeric carbon, disaccharides thereof presenting or not a linker bound at the anomeric carbon of the reducing end monosaccharide, trisaccharides thereof presenting or not a linker bound at the anomeric carbon of the reducing end monosaccharide, and tetrasaccharides thereof presenting or not a linker bound at the anomeric carbon of the reducing end monosaccharide.

Still more preferably, the database of step B) contains or comprises at least entries for the above-mentioned monosaccharides, α- and β-pyranosides and furanosides thereof presenting a linker bound at the anomeric carbon, disaccharides thereof presenting or not a linker bound at the anomeric carbon of the reducing end monosaccharide, trisaccharides thereof presenting or not a linker bound at the anomeric carbon of the reducing end monosaccharide, tetrasaccharides thereof presenting or not a linker bound at the anomeric carbon of the reducing end monosaccharide, and pentasaccharides thereof presenting or not a linker bound at the anomeric carbon of the reducing end monosaccharide.

When considering the monosaccharide D-Glc, the term "α- and β-pyranosides and furanosides thereof presenting a linker bound at the anomeric carbon" encompasses for the case where the linker has the following structure: —O—$(CH_2)_n$—$NH_2$, the following structures: α-D-Glcp-O—$(CH_2)_n$—$NH_2$, β-D-Glcp-O—$(CH_2)_n$—$NH_2$, α-D-Glcf-O—$(CH_2)_n$—$NH_2$, β-D-Glcf-O—$(CH_2)_n$—$NH_2$.

When considering the monosaccharides D-Glc and D-Gal, the term "disaccharides thereof presenting a linker bound at the anomeric carbon of the reducing end monosaccharide" encompasses for the case where the linker has the following structure: —O—$(CH_2)_n$—$NH_2$, the following structures:

I) α-D-Glcp-(1→2)-α-D-Galp-O—$(CH_2)_n$—$NH_2$, α-D-Glcp-(1→3)-α-D-Galp-O—$(CH_2)_n$—$NH_2$, α-D-Glcp-(1→4)-α-D-Galp-O—$(CH_2)_n$—$NH_2$, α-D-Glcp-(1→6)-α-D-Galp-O—$(CH_2)_n$—$NH_2$, α-D-Glcp-(1→2)-β-D-Galp-O—$(CH_2)_n$—$NH_2$, α-D-Glcp-(1→3)-β-D-Galp-O—$(CH_2)_n$—$NH_2$, α-D-Glcp-(1→4)-β-D-Galp-O—$(CH_2)_n$—$NH_2$, α-D-Glcp-(1→6)-β-D-Galp-O—$(CH_2)_n$—$NH_2$, β-D-Glcp-(1→2)-β-D-Galp-O—$(CH_2)_n$—$NH_2$, β-D-Glcp-(1→3)-β-D-Galp-O—$(CH_2)_n$—$NH_2$, β-D-Glcp-(1→4)-β-D-Galp-O—$(CH_2)_n$—$NH_2$, β-D-Glcp-(1→6)-β-D-Galp-O—$(CH_2)_n$—$NH_2$, β-D-Glcp-(1→2)-α-D-Galp-O—$(CH_2)_n$—$NH_2$, β-D-Glcp-(1→3)-α-D-Galp-O—$(CH_2)_n$—$NH_2$, β-D-Glcp-(1→4)-α-D-Galp-O—$(CH_2)_n$—$NH_2$, β-D-Glcp-(1→6)-α-D-Galp-O—$(CH_2)_n$—$NH_2$, α-D-Galp-(1→2)-α-D-Glcp-O—$(CH_2)_n$—$NH_2$, α-D-Galp-(1→3)-α-D-Glcp-O—$(CH_2)_n$—$NH_2$, α-D-Galp-(1→4)-α-D-Glcp-O—$(CH_2)_n$—$NH_2$, α-D-Galp-(1→6)-α-D-Glcp-O—$(CH_2)_n$—$NH_2$, α-D-Galp-(1→2)-β-D-Glcp-O—$(CH_2)_n$—$NH_2$, α-D-Galp-(1→3)-β-D-Glcp-O—$(CH_2)_n$—$NH_2$, α-D-Galp-(1→4)-β-D-Glcp-O—$(CH_2)_n$—$NH_2$, α-D-Galp-(1→6)-β-D-Glcp-O—$(CH_2)_n$—$NH_2$, β-D-Galp-(1→2)-β-D-Glcp-O—$(CH_2)_n$—$NH_2$, β-D-Galp-(1→3)-β-D-Glcp-O—$(CH_2)_n$—$NH_2$, β-D-Galp-(1→4)-β-D-Glcp-O—$(CH_2)_n$—$NH_2$, β-D-Galp-(1→6)-β-D-Glcp-O—$(CH_2)_n$—$NH_2$, β-D-Galp-(1→2)-α-D-Glcp-O—$(CH_2)_n$—$NH_2$, β-D-Galp-(1→3)-α-D-Glcp-O—$(CH_2)_n$—$NH_2$, β-D-Galp-(1→4)-α-D-Glcp-O—$(CH_2)_n$—$NH_2$, β-D-Galp-(1→6)-α-D-Glcp-O—$(CH_2)_n$—$NH_2$, α-D-Glcf-(1→2)-α-D-Galp-O—$(CH_2)_n$—$NH_2$, α-D-Glcf-(1→3)-α-D-Galp-O—$(CH_2)_n$—$NH_2$, α-D-Glcf-(1→4)-α-D-Galp-O—$(CH_2)_n$—$NH_2$, α-D-Glcf-(1→6)-α-D-Galp-O—$(CH_2)_n$—$NH_2$, α-D-Glcf-(1→2)-β-D-Galp-O—$(CH_2)_n$—$NH_2$, α-D-Glcf-(1→3)-β-D-Galp-O—$(CH_2)_n$—$NH_2$, α-D-Glcf-(1→4)-β-D-Galp-O—$(CH_2)_n$—$NH_2$, α-D-Glcf-(1→6)-β-D-Galp-O—$(CH_2)_n$—$NH_2$, β-D-Glcf-(1→2)-β-D-Galp-O—$(CH_2)_n$—$NH_2$, β-D-Glcf-(1→3)-β-D-Galp-O—$(CH_2)_n$—$NH_2$, β-D-Glcf-(1→4)-β-D-Galp-O—$(CH_2)_n$—$NH_2$, β-D-Glcf-(1→6)-β-D-Galp-O—$(CH_2)_n$—$NH_2$, β-D-Glcf-(1→2)-α-D-Galp-O—$(CH_2)_n$—$NH_2$, β-D-Glcf-(1→3)-α-D-Galp-O—$(CH_2)_n$—$NH_2$, β-D-Glcf-(1→4)-α-D-Galp-O—$(CH_2)_n$—$NH_2$, β-D-Glcf-(1→6)-α-D-Galp-O—$(CH_2)_n$—$NH_2$, α-D-Glcp-(1→2)-α-D-Glcp-O—$(CH_2)_n$—$NH_2$, α-D-Glcp-(1→3)-α-D-Glcp-O—$(CH_2)_n$—$NH_2$, α-D-Glcp-(1→4)-α-D-Glcp-O—$(CH_2)_n$—$NH_2$, α-D-Glcp-(1→6)-α-D-Glcp-O—$(CH_2)_n$—$NH_2$, α-D-Glcp-(1→2)-β-D-Glcp-O—$(CH_2)_n$—$NH_2$, α-D-Glcp-(1→3)-β-D-Glcp-O—$(CH_2)_n$—$NH_2$, α-D-Glcp-(1→4)-β-D-Glcp-O—$(CH_2)_n$—$NH_2$, α-D-Glcp-(1→6)-β-D-Glcp-O—$(CH_2)_n$—$NH_2$, β-D-Glcp-(1→2)-β-D-Glcp-O—$(CH_2)_n$—$NH_2$, β-D-Glcp-(1→3)-β-D-Glcp-O—$(CH_2)_n$—$NH_2$, β-D-Glcp-(1→4)-β-D-Glc-O—$(CH_2)_n$—$NH_2$, β-D-Glcp-(1→6)-β-D-Glcp-O—$(CH_2)_n$—$NH_2$, β-D-Glcp-(1→2)-α-D-Glcp-O—$(CH_2)_n$—$NH_2$, β-D-Glcp-(1→3)-α-D-Glcp-O—$(CH_2)_n$—$NH_2$, β-D-Glcp-(1→4)-α-D-Glcp-O—$(CH_2)_n$—$NH_2$, β-D-Glcp-(1→6)-α-D-Glcp-O—$(CH_2)_n$—$NH_2$, α-D-Galp-(1→2)-α-D-Galp-O—$(CH_2)_n$—$NH_2$, α-D-Galp-(1→3)-α-D-Galp-O—$(CH_2)_n$—$NH_2$, α-D-Galp-(1→4)-α-D-Galp-O—$(CH_2)_n$—$NH_2$, α-D-Galp-(1→6)-α-D-Galp-O—$(CH_2)_n$—$NH_2$, α-D-Galp-(1→2)-β-D-Galp-O—$(CH_2)_n$—$NH_2$, α-D-Galp-(1→3)-β-D-Galp-O—$(CH_2)_n$—$NH_2$, α-D-Galp-(1→4)-β-D-Galp-O—$(CH_2)_n$—$NH_2$, α-D-Galp-(1→6)-β-D-Galp-O—$(CH_2)_n$—$NH_2$, β-D-Galp-(1→2)-β-D-Galp-O—$(CH_2)_n$—$NH_2$, β-D-Galp-(1→3)-β-D-Galp-O—$(CH_2)_n$—$NH_2$, β-D-Galp-(1→4)-β-D-Galp-O—$(CH_2)_n$—$NH_2$, β-D-Galp-(1→6)-β-D-Galp-O—$(CH_2)_n$—$NH_2$, β-D-Galp-(1→2)-α-D-Galp-O—$(CH_2)_n$—$NH_2$, β-D-Galp-(1→3)-α-D-Galp-O—$(CH_2)_n$—$NH_2$, β-D-Galp-(1→4)-α-D-Galp-O—$(CH_2)_n$—$NH_2$, β-D-Galp-(1→6)-α-D-Galp-O—$(CH_2)_n$—$NH_2$, α-D-Glcf-(1→2)-α-D-Galf-O—$(CH_2)_n$—$NH_2$, α-D-Glcf-(1→3)-α-D-Galf-O—$(CH_2)_n$—$NH_2$, α-D-Glcf-(1→5)-α-D-Galf-O—$(CH_2)_n$—$NH_2$, α-D-Glcf-(1→6)-α-D-Galf-O—$(CH_2)_n$—$NH_2$, α-D-Glcf-(1→2)-β-D-Galf-O—$(CH_2)_n$—$NH_2$, α-D-Glcf-(1→3)-β-D-Galf-O—$(CH_2)_n$—$NH_2$, α-D-Glcf-(1→5)-β-D-Galf-O—$(CH_2)_n$—$NH_2$, α-D-Glcf-(1→6)-β-D-Galf-O—$(CH_2)_n$—$NH_2$, β-D-Glcf-(1→2)-β-D-Galf-O—$(CH_2)_n$—$NH_2$, β-D-Glcf-(1→3)-β-D-Galf-O—$(CH_2)_n$—$NH_2$, β-D-Glcf-(1→5)-β-D-Galf-O—$(CH_2)_n$—$NH_2$, β-D-Glcf-(1→6)-β-D-Galf-O—$(CH_2)_n$—$NH_2$, β-D-Glcf-(1→2)-α-D-Galf-O—$(CH_2)_n$—$NH_2$, β-D-Glcf-(1→3)-α-D-Galf-O—$(CH_2)_n$—$NH_2$, β-D-Glcf-(1→5)-α-D-Galf-O—$(CH_2)_n$—$NH_2$, β-D-Glcf-(1→6)-α-D-Galf-O—$(CH_2)_n$—$NH_2$, α-D-Glcf-(1→2)-α-D-Glcf-O—$(CH_2)_n$—$NH_2$, α-D-Glcf-(1→3)-α-D-Glcf-O—$(CH_2)_n$—$NH_2$, α-D-Glcf-(1→5)-α-D-Glcf-O—$(CH_2)_n$—$NH_2$, α-D-Glcf- (1→6)-α-D-Glcf-O—(CH$_2$)$_n$—NH$_2$, α-D-Glcf-(1→2)-β-D-Glcf-O—(CH$_2$)$_n$—NH$_2$, α-D-Glcf-(1→3)-β-D-Glcf-O—(CH$_2$)$_n$—NH$_2$, α-D-Glcf-(1→5)-β-D-Glcf-O—(CH$_2$)$_n$—NH$_2$, α-D-Glcf-(1→6)-β-D-Glcf-O—(CH$_2$)$_n$—NH$_2$, β-D-Glcf-(1→2)-β-D-Glcf-O—(CH$_2$)$_n$—NH$_2$, β-D-Glcf-(1→3)-β-D-Glcf-O—(CH$_2$)$_n$—NH$_2$, β-D-Glcf-(1→5)-β-D-Glcf-O—(CH$_2$)$_n$—NH$_2$, β-D-Glcf-(1→6)-β-D-Glcf-O—(CH$_2$)$_n$—NH$_2$, β-D-Glcf-(1→2)-α-D-Glcf-O—(CH$_2$)$_n$—NH$_2$, β-D-Glcf-(1→3)-α-D-Glcf-O—(CH$_2$)$_n$—NH$_2$, β-D-Glcf-(1→5)-α-D-Glcf-O—(CH$_2$)$_n$—NH$_2$, β-D-Glcf-(1→6)-α-D-Glcf-O—(CH$_2$)$_n$—NH$_2$, α-D-Galf-(1→2)-α-D-Galf-O—(CH$_2$)$_n$—NH$_2$, α-D-Galf-(1→3)-α-D-Galf-O—(CH$_2$)$_n$—NH$_2$, α-D-Galf-(1→5)-α-D-Galf-O—(CH$_2$)$_n$—NH$_2$, α-D-Galf-(1→6)-α-D-Galf-O—(CH$_2$)$_n$—NH$_2$, α-D-Galf-(1→2)-β-D-Galf-O—(CH$_2$)$_n$—NH$_2$, α-D-Galf-(1→3)-β-D-Galf-O—(CH$_2$)$_n$—NH$_2$, α-D-Galf-(1→5)-β-D-Galf-O—(CH$_2$)$_n$—NH$_2$, α-D-Galf-(1→6)-β-D-Galf-O—(CH$_2$)$_n$—NH$_2$, β-D-Galf-(1→2)-β-D-Galf-O—(CH$_2$)$_n$—NH$_2$, β-D-Galf-(1→3)-β-D-Galf-O—(CH$_2$)$_n$—NH$_2$, β-D-Galf-(1→5)-β-D-Galf-O—(CH$_2$)$_n$—NH$_2$, β-D-Galf-(1→6)-β-D-Galf-O—(CH$_2$)$_n$—NH$_2$, β-D-Galf-(1→2)-α-D-Galf-O—(CH$_2$)$_n$—NH$_2$, β-D-Galf-(1→3)-α-D-Galf-O—(CH$_2$)$_n$—NH$_2$, β-D-Galf-(1→5)-α-D-Galf-O—(CH$_2$)$_n$—NH$_2$, β-D-Galf-(1→6)-α-D-Galf-O—(CH$_2$)$_n$—NH$_2$, α-D-Galf-(1→2)-α-D-Glcp-O—(CH$_2$)$_n$—NH$_2$, α-D-Galf-(1→3)-α-D-Glcp-O—(CH$_2$)$_n$—NH$_2$, α-D-Galf-(1→4)-α-D-Glcp-O—(CH$_2$)$_n$—NH$_2$, α-D-Galf-(1→6)-α-D-Glcp-O—(CH$_2$)$_n$—NH$_2$, α-D-Galf-(1→2)-β-D-Glcp-O—(CH$_2$)$_n$—NH$_2$, α-D-Galf-(1→3)-β-D-Glcp-O—(CH$_2$)$_n$—NH$_2$, α-D-Galf-(1→4)-β-D-Glcp-O—(CH$_2$)$_n$—NH$_2$, α-D-Galf-(1→6)-β-D-Glcp-O—(CH$_2$)$_n$—NH$_2$, β-D-Galf-(1→2)-β-D-Glcp-O—(CH$_2$)$_n$—NH$_2$, β-D-Galf-(1→3)-β-D-Glcp-O—(CH$_2$)$_n$—NH$_2$, β-D-Galf-(1→4)-β-D-Glcp-O—(CH$_2$)$_n$—NH$_2$, β-D-Galf-(1→6)-β-D-Glcp-O—(CH$_2$)$_n$—NH$_2$, β-D-Galf-(1→2)-α-D-Glcp-O—(CH$_2$)$_n$—NH$_2$, β-D-Galf-(1→3)-α-D-Glcp-O—(CH$_2$)$_n$—NH$_2$, β-D-Galf-(1→4)-α-D-Glcp-O—(CH$_2$)$_n$—NH$_2$, β-D-Galf-(1→6)-α-D-Glcp-O—(CH$_2$)$_n$—NH$_2$, α-D-Galp-(1→2)-α-D-Glcf-O—(CH$_2$)$_n$—NH$_2$, α-D-Galp-(1→3)-α-D-Glcf-O—(CH$_2$)$_n$—NH$_2$, α-D-Galp-(1→5)-α-D-Glcf-O—(CH$_2$)$_n$—NH$_2$, α-D-Galp-(1→6)-α-D-Glcf-O—(CH$_2$)$_n$—NH$_2$, α-D-Galp-(1→2)-β-D-Glcf-O—(CH$_2$)$_n$—NH$_2$, α-D-Galp-(1→3)-β-D-Glcf-O—(CH$_2$)$_n$—NH$_2$, α-D-Galp-(1→5)-β-D-Glcf-O—(CH$_2$)$_n$—NH$_2$, α-D-Galp-(1→6)-β-D-Glcf-O—(CH$_2$)$_n$—NH$_2$, β-D-Galp-(1→2)-β-D-Glcf-O—(CH$_2$)$_n$—NH$_2$, β-D-Galp-(1→3)-β-D-Glcf-O—(CH$_2$)$_n$—NH$_2$, β-D-Galp-(1→5)-β-D-Glcf-O—(CH$_2$)$_n$—NH$_2$, β-D-Galp-(1→6)-β-D-Glcf-O—(CH$_2$)$_n$—NH$_2$, β-D-Galp-(1→2)-α-D-Glcf-O—(CH$_2$)$_n$—NH$_2$, β-D-Galp-(1→3)-α-D-Glcf-O—(CH$_2$)$_n$—NH$_2$, β-D-Galp-(1→5)-α-D-Glcf-O—(CH$_2$)$_n$—NH$_2$, β-D-Galp-(1→6)-α-D-Glcf-O—(CH$_2$)$_n$—NH$_2$, α-D-Galf-(1→2)-α-D-Glcf-O—(CH$_2$)$_n$—NH$_2$, α-D-Galf-(1→3)-α-D-Glcf-O—(CH$_2$)$_n$—NH$_2$, α-D-Galf-(1→5)-α-D-Glcf-O—(CH$_2$)$_n$—NH$_2$, α-D-Galf-(1→6)-α-D-Glcf-O—(CH$_2$)$_n$—NH$_2$, α-D-Galf-(1→2)-β-D-Glcf-O—(CH$_2$)$_n$—NH$_2$, α-D-Galf-(1→3)-β-D-Glcf-O—(CH$_2$)$_n$—NH$_2$, α-D-Galf-(1→5)-β-D-Glcf-O—(CH$_2$)$_n$—NH$_2$, α-D-Galf-(1→6)-β-D-Glcf-O—(CH$_2$)$_n$—NH$_2$, β-D-Galf-(1→2)-β-D-Glcf-O—(CH$_2$)$_n$—NH$_2$, β-D-Galf-(1→3)-β-D-Glcf-O—(CH$_2$)$_n$—NH$_2$, β-D-Galf-(1→5)-β-D-Glcf-O—(CH$_2$)$_n$—NH$_2$, β-D-Galf-(1→6)-β-D-Glcf-O—(CH$_2$)$_n$—NH$_2$, β-D-Galf-(1→2)-α-D-Glcf-O—(CH$_2$)$_n$—NH$_2$, β-D-Galf-(1→3)-α-D-Glcf-O—(CH$_2$)$_n$—NH$_2$, β-D-Galf-(1→5)-α-D-Glcf-O—(CH$_2$)$_n$—NH$_2$, β-D-Galf-(1→6)-α-D-Glcf-O—(CH$_2$)$_n$—NH$_2$, α-D-Glcp-(1→2)-α-D-Galf-O—(CH$_2$)$_n$—NH$_2$, α-D-Glcp-(1→3)-α-D-Galf-O—(CH$_2$)$_n$—NH$_2$, α-D-Glcp-(1→5)-α-D-Galf-O—(CH$_2$)$_n$—NH$_2$, α-D-Glcp-(1→6)-α-D-Galf-O—(CH$_2$)$_n$—NH$_2$, α-D-Glcp-(1→2)-β-D-Galf-O—(CH$_2$)$_n$—NH$_2$, α-D-Glcp-(1→3)-β-D-Galf-O—(CH$_2$)$_n$—NH$_2$, α-D-Glcp-(1→5)-β-D-Galf-O—(CH$_2$)$_n$—NH$_2$, α-D-Glcp-(1→6)-β-D-Galf-O—(CH$_2$)$_n$—NH$_2$, β-D-Glcp-(1→2)-β-D-Galf-O—(CH$_2$)$_n$—NH$_2$, β-D-Glcp-(1→3)-β-D-Galf-O—(CH$_2$)$_n$—NH$_2$, β-D-Glcp-(1→5)-β-D-Galf-O—(CH$_2$)$_n$—NH$_2$, β-D-Glcp-(1→6)-β-D-Galf-O—(CH$_2$)$_n$—NH$_2$, β-D-Glcp-(1→2)-α-D-Galf-O—(CH$_2$)$_n$—NH$_2$, β-D-Glcp-(1→3)-α-D-Galf-O—(CH$_2$)$_n$—NH$_2$, β-D-Glcp-(1→5)-α-D-Galf-O—(CH$_2$)$_n$—NH$_2$, β-D-Glcp-(1→6)-α-D-Galf-O—(CH$_2$)$_n$—NH$_2$.

Surprisingly, it was found that the method of the present invention, which uses ion mobility-mass spectrometry in negative mode ionization and fragmentation enables the determination of the stereochemistry of each of the anomeric carbons of the target carbohydrate. This is the first IM-MS based method that enables the assignment of the stereochemistry for all the anomeric carbons of a target saccharide or unknown saccharide.

Besides determining the stereochemistry of each of the anomeric carbons of the target carbohydrate, the present method enables determination of the compositional structure of the target carbohydrate, as well as linkage connectivity between the monosaccharides. As demonstrated for example by FIGS. 3, 7 and 9, the method described herein even enables the differentiation of structurally closed target carbohydrates, such as diastereoisomers including those differing only through the stereochemistry of one chiral center, such as anomers, and glycosidic linkage regioisomers (for e.g. 1→2 versus 1→3 connection of the same monosaccharides).

Preferably, the inventive method further comprises step G), which is performed after step F):

G) storing the structure of the target carbohydrate determined at step F) and the collision cross section value determined at step D) and mass-to-charge ratio value determined at step C) of the negative ion thereof in the database.

Including in the database, the structure of a newly identified target carbohydrate (i.e. a target carbohydrate whose structure is not contained in the database and was determined following the method described herein and using the entries corresponding to its fragments, which were stored in the database), the collision cross section value and the mass-to-charge ratio value of the negative ion thereof, supports the development of the database and thereby, renders expedient and unambiguous the determination of the structure of a target carbohydrate.

It is preferred that the negative ion of the target carbohydrate for which the drift time value and the mass-to-charge ratio value is determined at step C) of the inventive method is selected from the group comprising the deprotonated ion of the target carbohydrate and the anion complex of the target carbohydrate with chloride (Cl$^-$), acetate (CH$_3$CO$_2^-$), monochloroacetate (CH$_2$ClCO$_2^-$), dichloroacetate (CHCl$_2$CO$_2^-$), trichloroacetate (CCl$_3$CO$_2^-$), trifluoroacetate (CF$_3$CO$_2^-$), formate (HCO$_2^-$), monobromoacetate (CH$_2$BrCO$_2^-$), dibromoacetate (CHBr$_2$CO$_2^-$), tribromoacetate (CBr$_3$CO$_2^-$), bromochloroacetate (CBrClHCO$_2^-$), chlorodibromoacetate (CClBr$_2$CO$_2^-$), bromodichloroacetate (CBrCl$_2$CO$_2^-$), nitrate (NO$_3^-$) or phosphate (H$_2$PO$_4^-$).

Even more preferred is that the negative ion of the target carbohydrate for which the drift time value and the mass-to-charge ratio value is measured at step C) of the inventive method is the deprotonated ion of the target carbohydrate. The method described herein is particularly useful when the drift time value of the deprotonated ion of the target carbohydrate and of the fragments of the deprotonated ion of the target carbohydrate is measured at step C) and step E2) of the method, respectively. The drift time values and the corresponding collision cross section values of the deprotonated ions enable an accurate differentiation between α/β anomers and regioisomers. In the case where a sample contains several target isobaric carbohydrates, a quantitative determination of the relative concentration ratio corresponding to each of isobaric target carbohydrates present in the sample can be achieved. Furthermore, even low amounts of target carbohydrate, such as less than 0.1% by weight in the analyte, can be detected. In such a case, high intensity measurements of the drift time value and m/z value enables the detection of the target carbohydrate and the determination of its structure (see FIG. 2).

The inventive method described herein allows the determination of the structure of any target carbohydrate or unknown carbohydrate. It is preferred that the target carbohydrate is a synthetic carbohydrate or a carbohydrate isolated from natural sources.

In a preferred embodiment the target carbohydrate whose structure is to be determined using the inventive method is a synthetic carbohydrate, which further comprises a linker covalently bound to the anomeric carbon of the reducing end monosaccharide of the synthetic carbohydrate. Currently, a variety of linkers that can be covalently bound to the anomeric carbon are available (see for example: WO 2015/004041 A1). The inventive method described herein allows the assignment or determination of the structure of a synthetic carbohydrate functionalized at the anomeric position with any of the linkers described in the prior art. FIG. 7 clearly illustrates that the present method enables the determination of the structure for carbohydrates presenting on the anomeric position a linker covalently bound to the anomeric carbon. Thus, the inventive method described herein also enables the determination of the structure of a target carbohydrate, wherein the target carbohydrate is a synthetic carbohydrate, which further comprises a linker covalently bound to the anomeric carbon of the reducing end monosaccharide of the synthetic carbohydrate, wherein the linker is selected from: —O—$(CH_2)_m$—$CH_3$, —O—$(CH_2)_n$—$NH_2$, —O—$(CH_2)_n$—SH, —O—$(CH_2$—$CH_2$—O$)_o$—$C_2H_4$—$NH_2$, —O—$(CH_2$—$CH_2$—O$)_o$—$C_2H_4$—$NH_2$, wherein m is an integer selected from 0, 1, 2, 3, 4, 5, 6, 7, 8, 9 and 10; n is an integer selected from 1, 2, 3, 4, 5, 6, 7, 8, 9 and 10; and o is an integer selected from 1, 2, 3, 4 and 5.

Hence, it is preferred that the database of step B) further comprises the structures of linkers that could be covalently bound to the anomeric carbon of the reducing end monosaccharide of a synthetic carbohydrate and for each of the structures the collision cross section value and the mass-to-charge ratio value of the negative ion thereof.

In a further preferred embodiment, the target carbohydrate is a carbohydrate isolated from natural sources such as an O-glycan, an N-glycan, a milk sugar, a bacterial oligo- or polysaccharide. Thus, by applying the inventive method described herein, the structure of any unknown saccharide can be assigned.

The target carbohydrate whose structure has to be determined comprises preferably between 1 and 50 monosaccharides, more preferably between 2 and 25 monosaccharides, and still more preferably between 3 and 10 monosaccharides The method of the present invention enables the detection of the target carbohydrate in the sample even at low concentration of 0.2 μg/mL (see FIG. 2). It is preferred that if the target carbohydrate has between 1 and 10 monosaccharides, its concentration in the sample provided at step A) is at least of 0.2 μg/mL. It is also preferred that if the target carbohydrate has between 11 and 50 monosaccharides, its concentration in the sample is at least of 1 μg/mL.

Preferably, the fragments generated at step E1) of the inventive method are generated using collision induced dissociation (CID), electron-transfer dissociation (ETD) or electron-capture dissociation (ECD) as fragmentation method.

In the case where the analyte is a mixture of several target carbohydrates, the structure of each of the target carbohydrates can be assigned. This is particularly useful for the assignment of the structure to each of the several isobaric carbohydrates present in an analyte.

It is further preferred that the sample containing the target carbohydrate provided at step A) further contains at least a further target carbohydrate, which is isobaric with the target carbohydrate. The wording "at least a further target carbohydrate, which is isobaric with the target carbohydrate" encompasses one isobaric target carbohydrate, two isobaric target carbohydrates, three isobaric target carbohydrates etc. In such case the analyte is a mixture of several isobaric target carbohydrates. In other words the analyte comprises or contains at least two isobaric target carbohydrates. Thus, the analyte can be a mixture of two isobaric target carbohydrates, or a mixture of three isobaric target carbohydrates or a mixture of four isobaric target carbohydrates etc. Once, the structure of each of the isobaric target carbohydrates present in an analyte is determined, it is possible to determine the relative concentration ratio of each of the target isobaric carbohydrates in the sample. As shown by FIG. 8, a linear correlation can be observed between the measured relative intensity and the relative concentration ratio for an isobaric target carbohydrate in a mixture of isobaric target carbohydrates. Hence, once the assignment of the structure to each of the isobaric carbohydrates present in an analyte is achieved, using graphs of the relative intensity in function of the relative concentration ratio, it is possible to quantitatively determine the relative concentration ratio of an isobaric target carbohydrate in a mixture of isobaric target carbohydrates.

As used herein, the term relative concentration ratio refers to the ratio between the relative concentration of one isobaric target carbohydrate and the sum of the relative concentration of all the isobaric carbohydrates present in an analyte.

Hence, the method described herein optionally comprises step H), which is performed after step F)

H) determining the relative concentration ratio of each of the target isobaric carbohydrates in the sample.

DESCRIPTION OF THE FIGURES

FIG. 1: Structural features of complex carbohydrates. The composition (I) is defined by the monosaccharide content. Monosaccharide building blocks are often isomers, as shown for glucose and galactose, which differ only in their C-4 stereochemistry. Due to the many functional groups, the formation of a new glycosidic bond can occur at several positions, resulting in different connectivities (II). Each glycosidic linkage is a new stereocenter that can have either α or β configuration (III).

Figure 2:
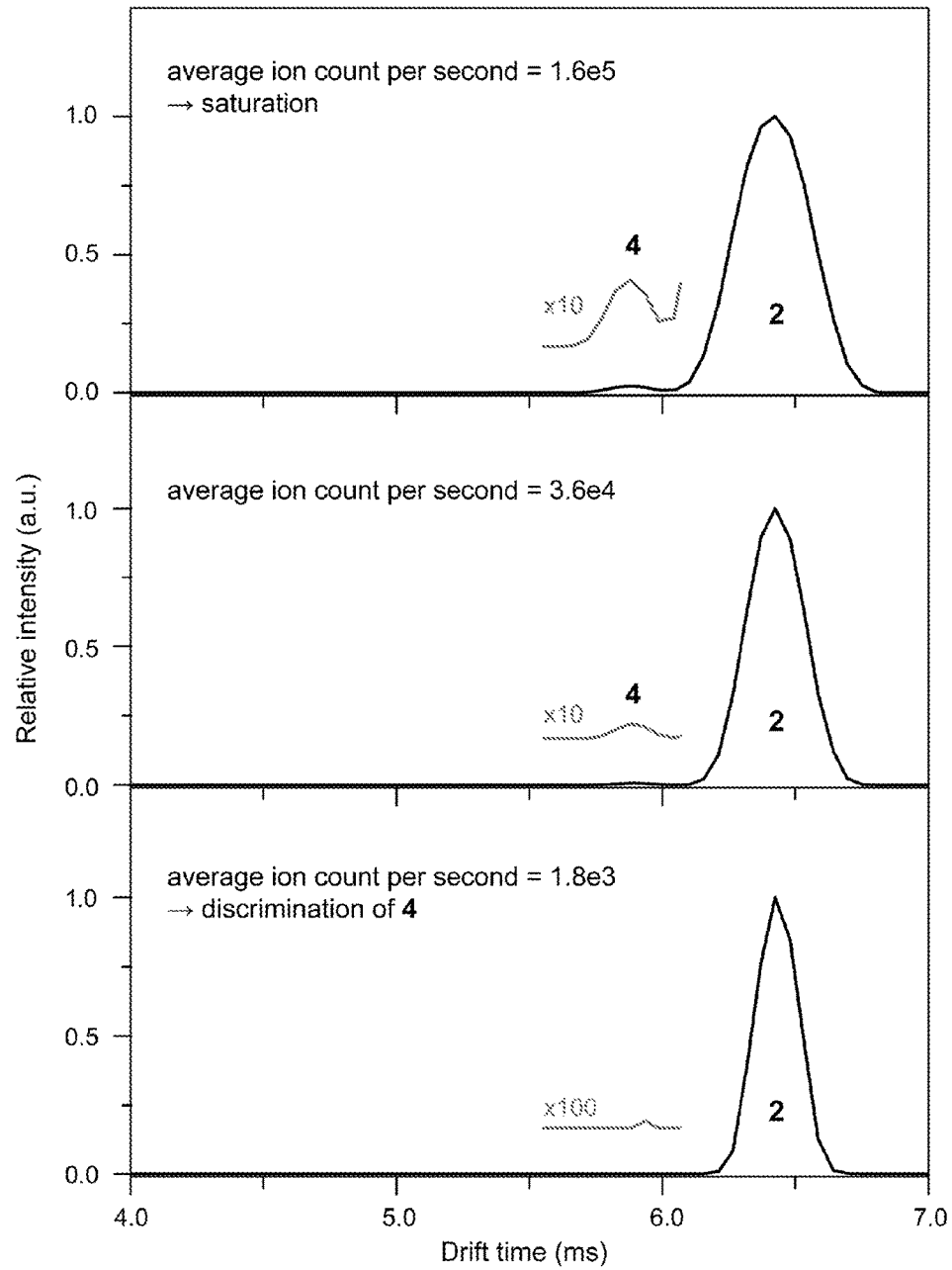
FIG. 2: Correlation between signal intensity and IM peak width in mixtures of 2 and 4. ATDs of [M-H]$^-$ ions from a mixture of <1% 4 and >99% 2. Measurements at high signal intensity can be used to qualitatively detect 4. At low intensity, however, 4 is discriminated leading to a signal, which is indistinguishable from the background.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

A) Analysis of Carbohydrates Using Ion Mobility-Mass Spectrometry:

Ion mobility-mass spectrometry (IM-MS) experiments were performed on a travelling wave quadrupole/IMS/oa-ToF MS instrument, Synapt G2-S HDMS (Waters, Manchester, U.K.) (Int. J. Mass Spectrom. 2007, 1-12), which was mass calibrated prior to measurements using a solution of cesium iodide (100 mg/mL). IM-MS data analysis was performed using MassLynx 4.1, DriftScope 2.4 (Waters, Manchester, UK), and OriginPro 8.5 (OriginLab Corporation, Northampton) software. For IM-MS analysis compounds 1-9, milk sugar lacto-N-tetraose (LNT, β-Gal-(1→3)-β-GlcNAc-(1→3)-β-Gal-(1×4)-Glc), milk sugar lacto-N-neo-tetraose (LNnT, β-Gal-(1→4)-β-GlcNAc-(1→3)-β-Gal-(1→4)-Glc), 33-37, the crude mixture 5/30 were each dissolved in water/methanol (1:1, v/v) to a concentration of 1-10 µmol/L.

TABLE 2
Structures of the saccharides analyzed by ion mobility-mass spectrometry in negative ionization mode.
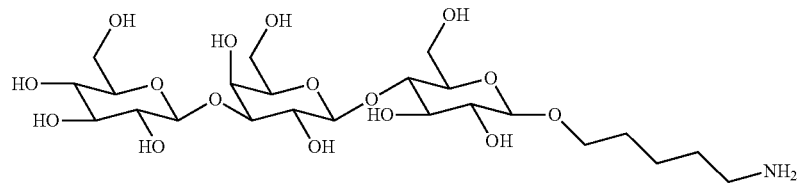 [SMILES: NCCCCCOC1OC(CO)C(OC2OC(CO)C(O)C(OC3OC(CO)C(O)C(O)C3O)C2O)C(O)C1O]
1
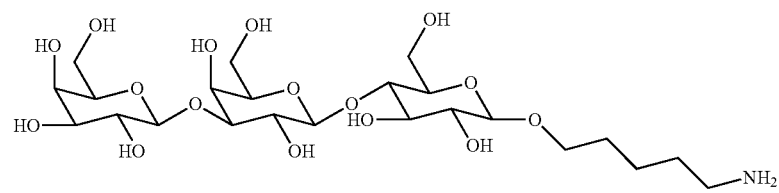 [SMILES: NCCCCCOC1OC(CO)C(OC2OC(CO)C(O)C(OC3OC(CO)C(O)C(O)C3O)C2O)C(O)C1O]
2
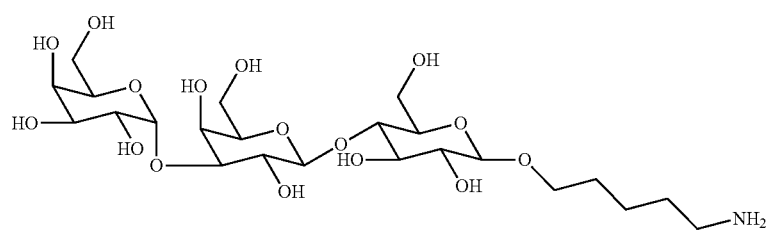 [SMILES: NCCCCCOC1OC(CO)C(OC2OC(CO)C(O)C(OC3OC(CO)C(O)C(O)C3O)C2O)C(O)C1O]
3
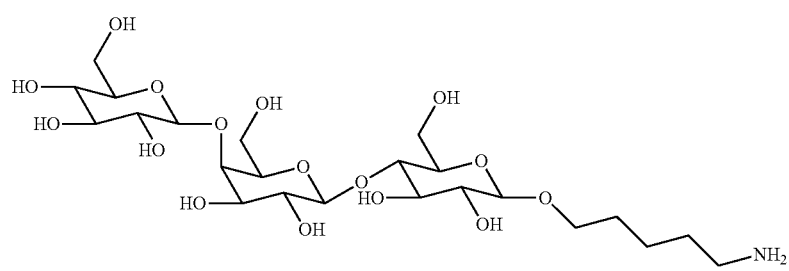 [SMILES: NCCCCCOC1OC(CO)C(OC2OC(CO)C(OC3OC(CO)C(O)C(O)C3O)C(O)C2O)C(O)C1O]
4
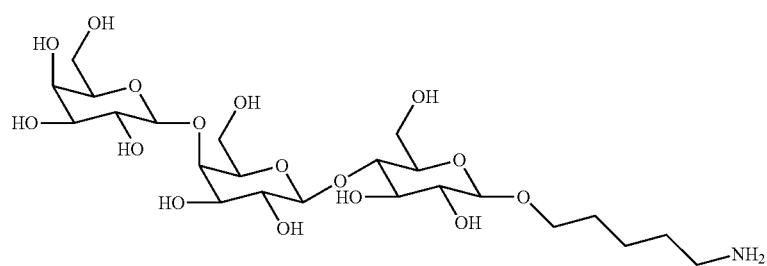 [SMILES: NCCCCCOC1OC(CO)C(OC2OC(CO)C(OC3OC(CO)C(O)C(O)C3O)C(O)C2O)C(O)C1O]
5
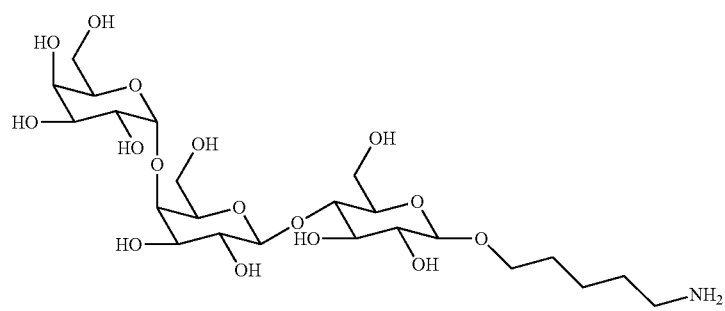 [SMILES: NCCCCCOC1OC(CO)C(OC2OC(CO)C(OC3OC(CO)C(O)C(O)C3O)C(O)C2O)C(O)C1O]
6

TABLE 2-continued
Structures of the saccharides analyzed by ion mobility-mass spectrometry in negative ionization mode.
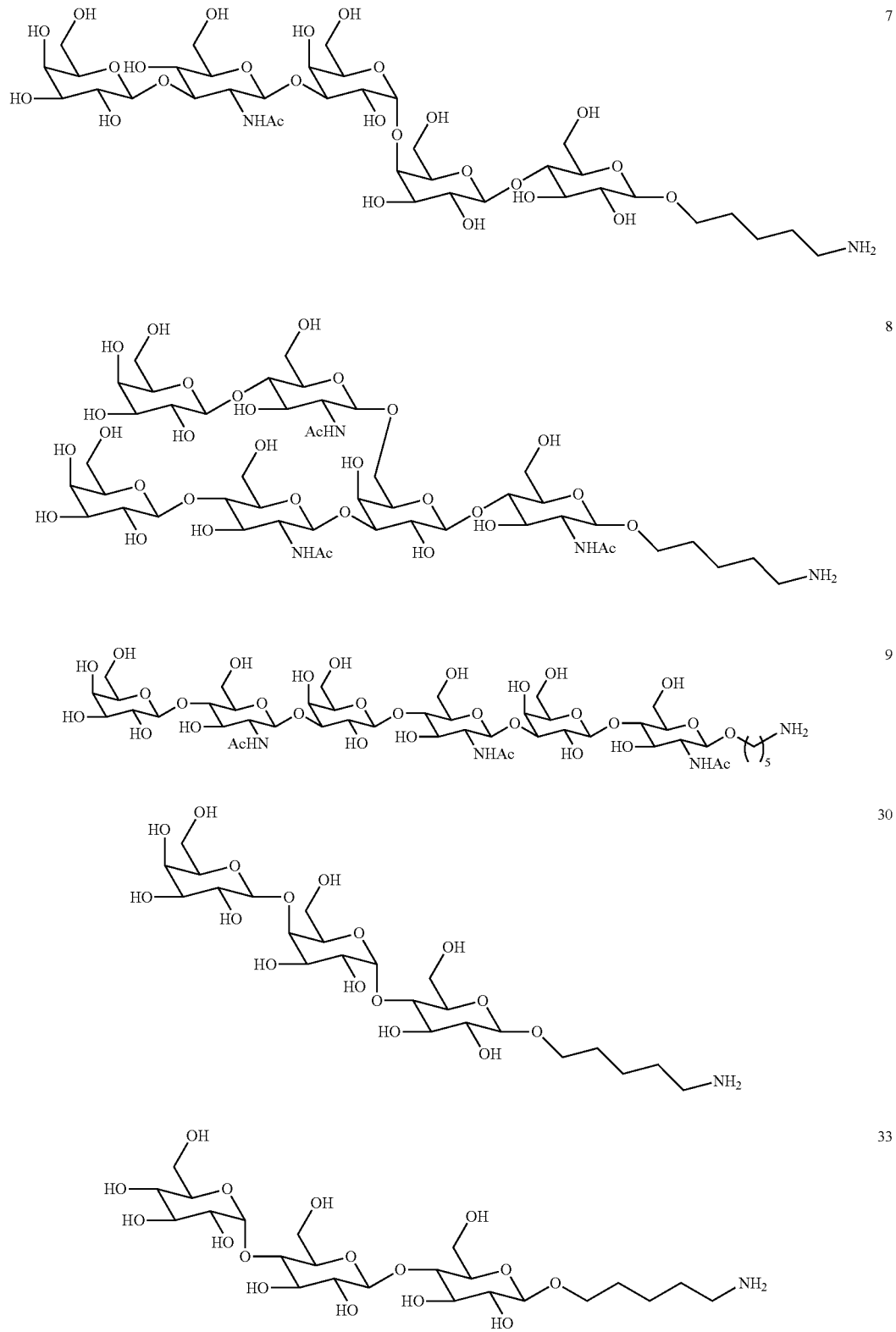

TABLE 2-continued

Structures of the saccharides analyzed by ion mobility-mass spectrometry in negative ionization mode.

35

36

37

A nano-electrospray source (nESI) was used to ionize 3-5 µL of sample from platinum-palladium-coated borosilicate capillaries prepared in-house. Typical settings were: source temperature, 20° C.; needle voltage, 0.8 kV; sample cone voltage, 25 V; cone gas, 0 L/h. The ion mobility parameters were optimized to achieve maximum resolution without excessive heating of the ions upon injection into the IM cell. Values were: trap gas flow, 2 mL/min; helium cell gas flow, 180 mL/min; IM gas flow, 90 mL/min; trap DC bias, 35 V; IM wave velocity, 800 m/s; IM wave height, 40 V. For MS/MS experiments the trap collision energy was increased to 30-60V.

IM-MS Spectra of each individual carbohydrate and three trisaccharide mixtures (6/3, 3/2 and 5/6) were recorded in negative ion mode. Arrival time distributions (ATD) were extracted from raw data using MassLynx and drift times were determined manually via Gaussian fitting using Origin 8.5. For the measurement of the individual carbohydrates, the m/z signal intensity was kept at approximately $10^3$ counts per second to avoid saturation and subsequent broadening of the corresponding drift peak. In order to avoid discrimination of a minor component, an average signal intensity of $10^4$ counts per second was used for the semi-quantitative assessment of mixtures (see FIG. 2). Under these conditions, minor components with relative concentrations below 1% can still be detected qualitatively, but a semi-quantitative assessment is no longer possible. For unknown mixtures, it is therefore required to acquire data at both high and low intensity settings. In the former case, minor components with relative concentrations below 1% can be qualitatively detected, while the latter case typically yields a better IM resolution and enables a semi-quantitative assessment (see FIG. 2). In addition, an acquisition at different intensity settings can help to evaluate mixtures in which the isomers cannot be fully resolved. For broad and inconclusive ATDs, a comparison with neighboring peaks of similar mass and charge can furthermore be used to distinguish between overlapping and saturated peaks. (*Anal. Chem.* 2013, 85, 5138-5145).

CCS estimations were performed using an established protocol and dextran as calibrant (Dextran MW=1000 and Dextran MW=5000, Sigma Aldrich) (*Anal. Chem.* 2013, 85, 5138-5145; *Anal. Chem.* 2014, 86, 10789-10795). The calibration solution consisted of 0.1 mg/mL dextran1000, 0.5 mg/mL dextran5000, and 1 mM $NaH_2PO_4$ in water:methanol (1:1, v/v). The calibrant and each sample were measured on a travelling wave Synapt instrument at five wave velocities in negative ion mode. Drift times where extracted from raw data by fitting a Gaussian distribution to the arrival time distribution of each ion and corrected for their m/z dependent flight time. CCS reference values of dextran were corrected for charge and mass and a logarithmic plot of corrected CCSs against corrected drift times was used as a calibration curve to estimate CCSs. One calibration curve was generated for every wave velocity and each ion polarity. The resulting five estimated CCSs for each sample ion were averaged. These measurements where repeated three times and the averaged values for different ions are presented in Table 3. The reported error corresponds to the standard deviation obtained for three independent replicates.

Figure 3:
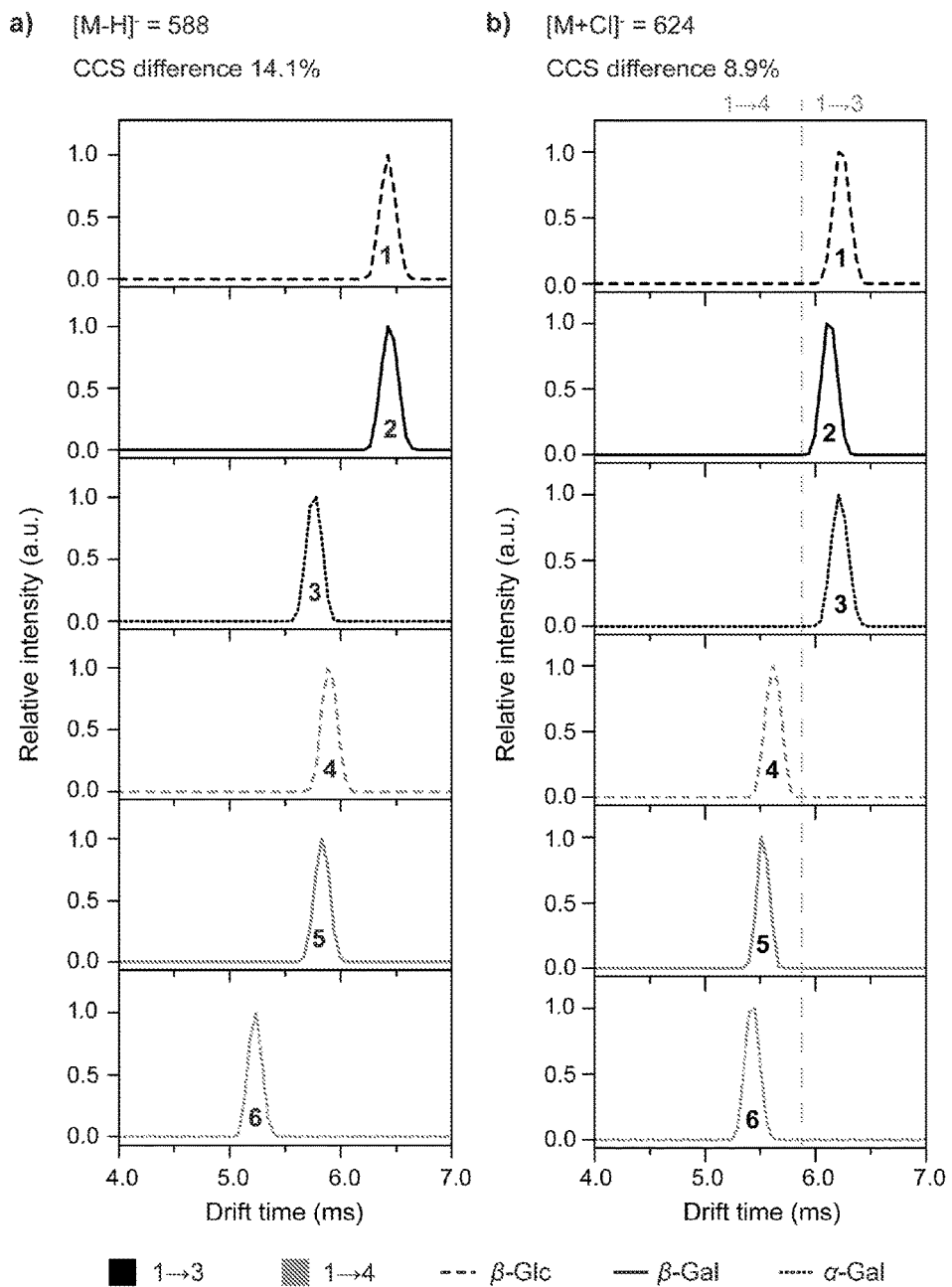
FIG. 3: Arrival time distributions of carbohydrates 1-6 as different species in negative ion mode: The difference in percent between the most compact and the most extended isomer of each negative ion is given in percent. The largest CCS differences can be achieved using deprotonated ions and allows for the identification of the regioisomers (e.g. 3/6) and anomers (e.g. 2/3). A clear identification of the regioisomers with a terminal 1→3 or 1→4 glycosidic bond can be obtained for chloride adducts.
Figure 4:
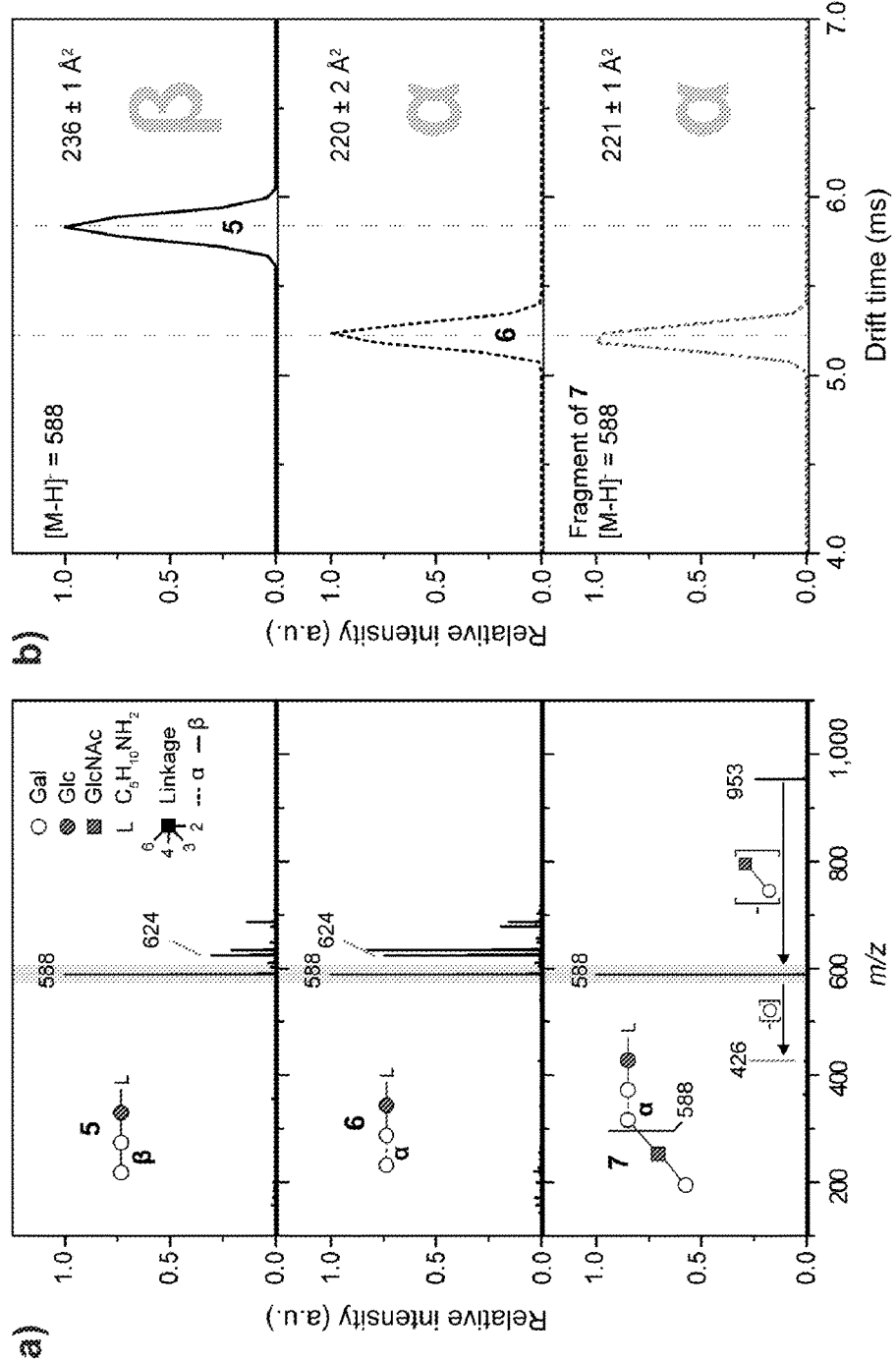
FIG. 4: Comparison of drift times and CCSs of structurally similar precursor ions and fragments. a) Mass spectra of 5 and 6, as well as MS/MS spectrum of 7 (β-Gal-(1→3)-β-GlcNAc-(1→3)-α-Gal-(1→4)-β-Gal-(1→4)-β-Glc-L; L=$C_5H_{10}NH_2$) in negative ion mode. The pentasaccharide 7 exhibits an identical core structure as the trisaccharide 6. CID of deprotonated 7 consequently leads to a fragment of identical mass as the deprotonated precursor ion of 6. b) Arrival time distributions of $[M-H]^-=588$ ions. The CID fragment arising from deprotonated 7 exhibits an identical drift time and CCS as the intact deprotonated trisaccharide 6. This indicates that glycans and glycan fragments with identical structure also exhibit identical CCSs.
Figure 5:
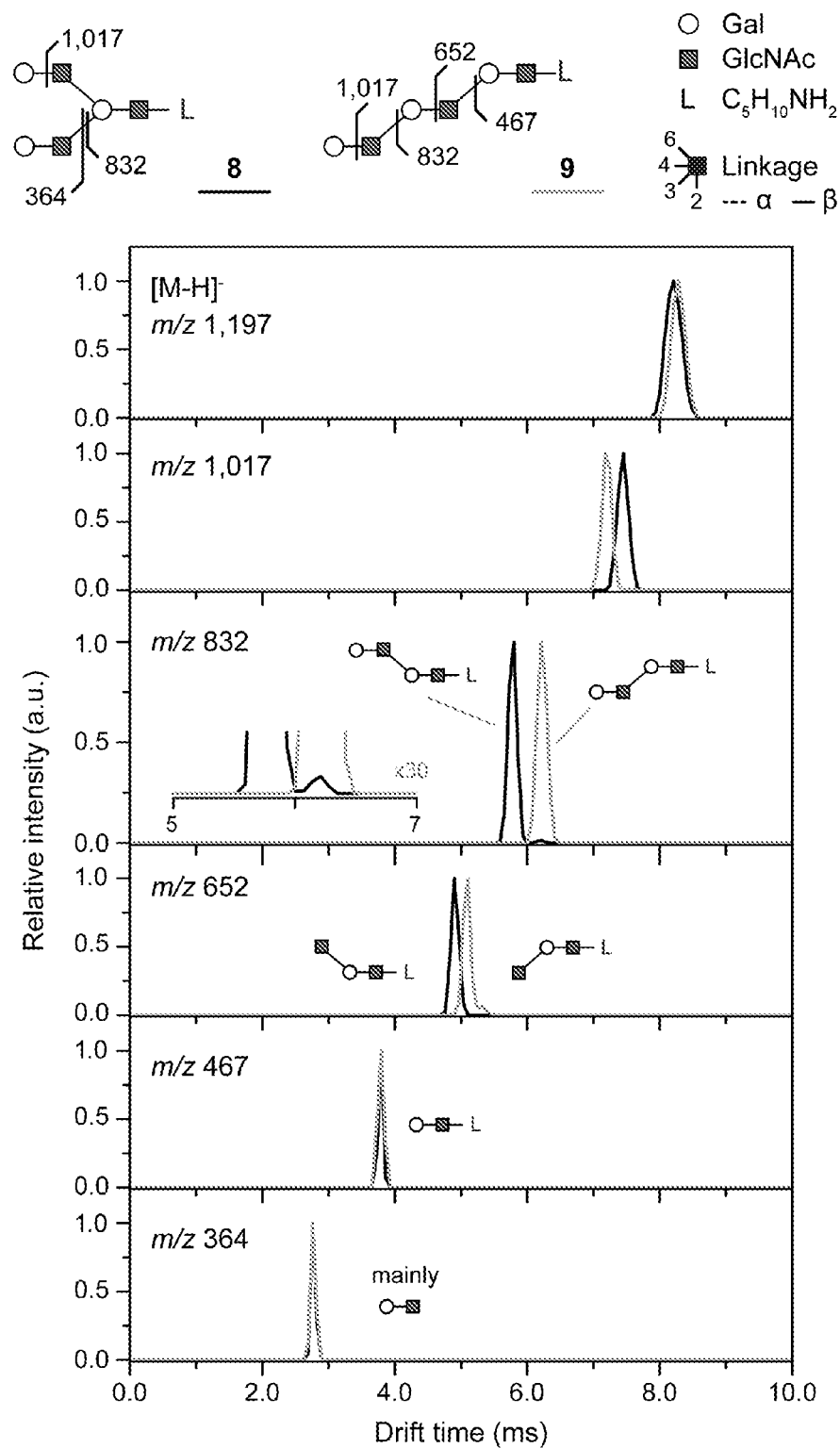
FIG. 5: IM-MS differentiation and identification of the larger hexasaccharides 8 and 9. Deprotonated ions 8 and 9 show almost identical drift times and therefore, cannot be distinguished. However, smaller CID fragments containing five, four, and three monosaccharide building blocks (m/z 1017, 832, and 652, respectively) exhibit highly diagnostic drift times. At m/z 832 a double peak is observed for the branched oligosaccharide 8 (inset, black trace), because two isomeric fragments are formed. Both fragments can be detected simultaneously using IM-MS with cleavage at the 3-antenna being clearly preferred. The disaccharide fragments at m/z 467 and 364 are identical for 8 and 9 and consequently exhibit identical drift times.
Figure 6:
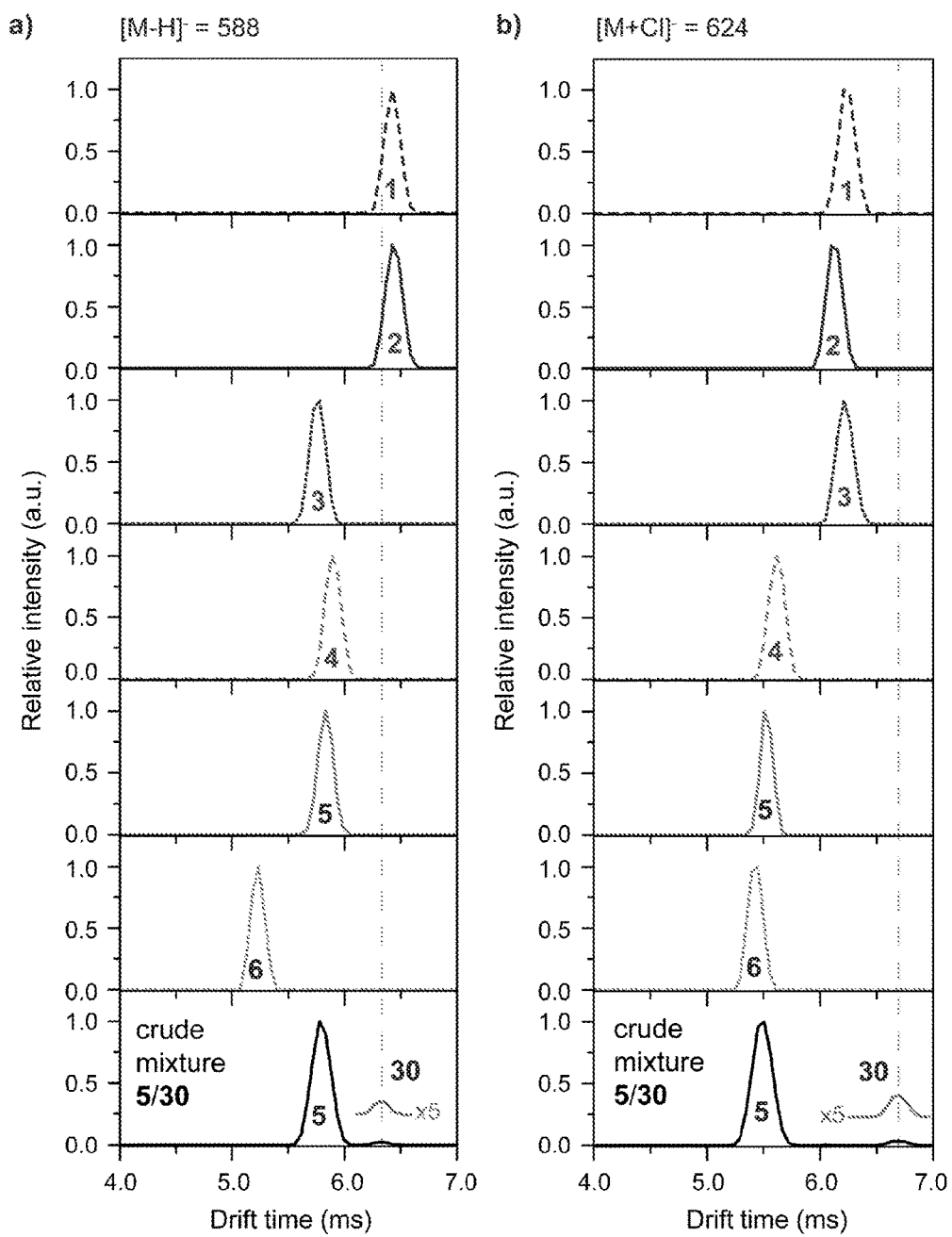
FIG. 6: IM-MS analysis of a mixture of two target carbohydrates. Arrival time distributions of the trisaccharides 1-6 compared to the mixture of 5 and 30 as a) $[M-H]^-=588$ and b) $[M+Cl]^-=624$ ions clearly reveals a content of about 5% of carbohydrate 30. Especially the drift time of the chloride adduct of 30 is very diagnostic, since it differs considerably from all other trisaccharides investigated here. Carbohydrate 30 could be detected by NMR, but due to the low concentration in the sample, an assignment of the structure cannot be performed.
Figure 7:
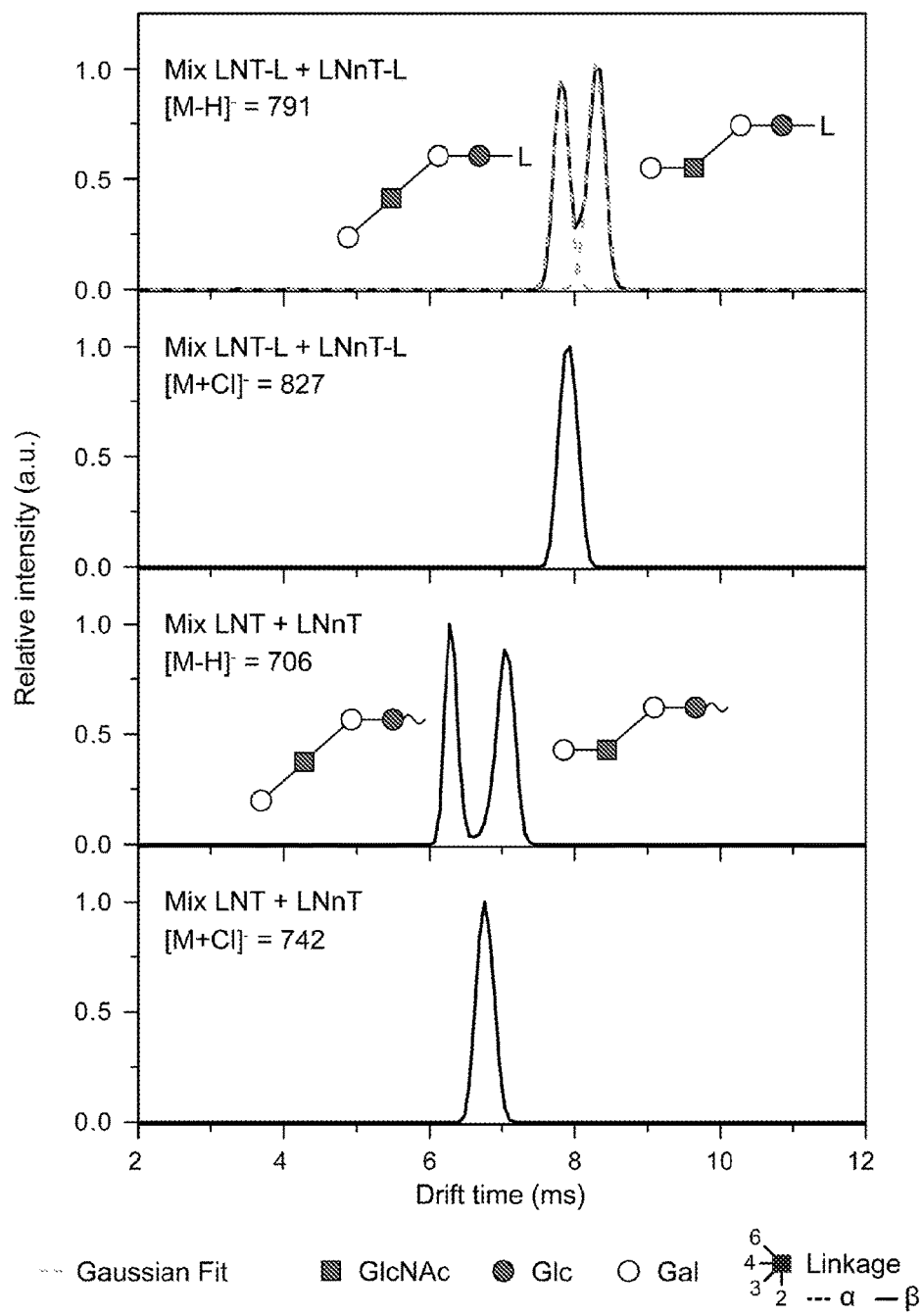
FIG. 7: Arrival time distributions (ATDs) of isomeric milk sugars with and without aminopentanol linker (L). To investigate the influence of a linker to the separation of carbohydrates, the milk sugars lacto-N-tetraose (LNT, β-Gal-(1→3)-β-GlcNAc-(1→3)-β-Gal-(1→4)-Glc) and lacto-N-neo-tetraose (LNnT, β-Gal-(1→4)-β-GlcNAc-(1→3)-β-Gal-(1→4)-Glc) were synthesized with and without an aminopentanol linker (L). Mixtures of both isomer pairs were analyzed in the negative ion mode using IM-MS. The ATDs of the chloride adducts show for both mixtures only one drift peak, which does not enable the separation of the milk sugars. However, the drift times of the deprotonated ions clearly differ and can be used to identify each isomer. The separation of the isomers was possible with and without the presence of a linker and thus indicates that the differences in drift time predominantly result from differences in carbohydrate structure.

FIG. 3 illustrates the arrival time distributions of target carbohydrates 1-6 as different species in negative ion mode. FIGS. 4 and 5 show how the assignment of the structure to large carbohydrates can be performed using the method described herein on the basis of the cross collisions values and the mass-to-charge ratios of the fragments of the negative ions thereof. FIG. 6 shows how the structure of each of the target carbohydrates contained in an analyte containing several target carbohydrates (herein the analyte is a mixture of 5 and 30) can be determined by using the inventive method. FIG. 7 illustrates that the current method enables the determination of the structure of carbohydrates functionalized or not with a linker at the anomeric position.

TABLE 3

Estimated nitrogen CCSs ($^{TW}CCS_{N2}$) for trisaccharides 1-6 and 30. Each $^{TW}CCS_{N2}$ is an average of three independent measurements with the corresponding standard deviation STD.

| Target Carbohydrate | Negative Ion | $^{TW}CCS_{N2}$ (Å$^2$) | STD (Å$^2$) | m/z | Negative Ion | $^{TW}CCS_{N2}$ (Å$^2$) | STD (Å$^2$) | m/z |
|---|---|---|---|---|---|---|---|---|
| 1 | [M − H]$^-$ | 294.4 | 1.1 | 588 | [M + Cl]$^-$ | 244.4 | 1.1 | 624 |
| 2 | [M − H]$^-$ | 249.8 | 1.5 | 588 | [M + Cl]$^-$ | 242.2 | 1.5 | 624 |
| 3 | [M − H]$^-$ | 233.2 | 1.3 | 588 | [M + Cl]$^-$ | 244.5 | 1.2 | 624 |
| 4 | [M − H]$^-$ | 237.4 | 0.9 | 588 | [M + Cl]$^-$ | 229.7 | 0.8 | 624 |
| 5 | [M − H]$^-$ | 235.6 | 1.0 | 588 | [M + Cl]$^-$ | 227.3 | 0.8 | 624 |
| 6 | [M − H]$^-$ | 219.9 | 1.6 | 588 | [M + Cl]$^-$ | 224.6 | 1.4 | 624 |
| 30 | [M − H]$^-$ | 248.4 | 0.3 | 588 | [M + Cl]$^-$ | 256.7 | 0.2 | 624 |

B) Semiquantitative Analysis of Carbohydrates Mixtures.

For the semiquantitative analysis of anomeric trisaccharide mixtures a quantification experiment was performed using isomers 2 and 3. Stock solutions of 2 and 3 with identical concentration were prepared in water/methanol (1:1, v/v). Each stock solution was diluted individually to yield relative concentrations (rel. conc.) of 80, 56, 43, 25, 11, 5, 1, 0.1, and 0.01%. The serial dilutions were used to obtain isomer mixtures with concentration ratios x(3)=c[3]/(c[2]+c[3]) between 0 and 1 (see Table 4). A value of 0.5 represents equal amounts of 2 and 3, while 0 and 1 indicate the presence of only 2 or 3, respectively.

TABLE 4

Relative concentrations of 2 and 3 in the investigated mixtures and their corresponding relative concentration ratio x(3) = [3]/[3 + 2]. Measured relative intensities Int$_{rel}$(3) = A[3]/(A[2] + A[3]) were calculated from the drift peak areas of the deprotonated species [M − H]$^-$ = 588.4 and the standard deviation (STD) was obtained from three independent replicates.

| rel. conc. 3 | rel. conc. 2 | theoretical x(3) | measured Int$_{rel}$(3) | STD |
|---|---|---|---|---|
| 1 | 100 | 0.01 | 0.04 | 0.011 |
| 5 | 100 | 0.05 | 0.07 | 0.004 |
| 11 | 100 | 0.10 | 0.10 | 0.007 |
| 25 | 100 | 0.20 | 0.18 | 0.005 |
| 43 | 100 | 0.30 | 0.27 | 0.005 |
| 56 | 100 | 0.36 | 0.35 | 0.005 |
| 80 | 100 | 0.44 | 0.42 | 0.010 |
| 100 | 100 | 0.50 | 0.49 | 0.007 |
| 100 | 80 | 0.56 | 0.55 | 0.016 |
| 100 | 56 | 0.64 | 0.60 | 0.005 |
| 100 | 43 | 0.70 | 0.69 | 0.008 |
| 100 | 25 | 0.80 | 0.78 | 0.005 |
| 100 | 11 | 0.90 | 0.89 | 0.010 |
| 100 | 5 | 0.95 | 0.93 | 0.012 |
| 100 | 1 | 0.99 | 0.97 | 0.007 |

To achieve constant experimental conditions, the semiquantitative analysis was performed on a Synapt instrument equipped with an online nano-ESI source that was coupled to an ACQUITY UPLC System (Waters, Manchester, U.K.). Settings were: eluents, 0.1% formic acid in methanol/0.1% formic acid in water at a constant rate of 50%, flow rate 8 μL/min, sample injection: 10 μL. Data were acquired in negative ion mode with following settings: source temperature, 80° C.; needle voltage, 2.7 kV; sample cone voltage, 25 V; desolvation temperature 150° C., 430 cone gas, 0 L/h, nanoflow gas 1.3 bar, purge gas flow 500.0 mL/h. Ion mobility parameter were: trap gas flow, 0.4 mL/min; helium cell gas flow, 180 mL/min; IM gas flow, 90 mL/min; trap DC bias, 45 V; IM wave velocity, 800 m/s; IM wave height, 40 V.

Figure 8:
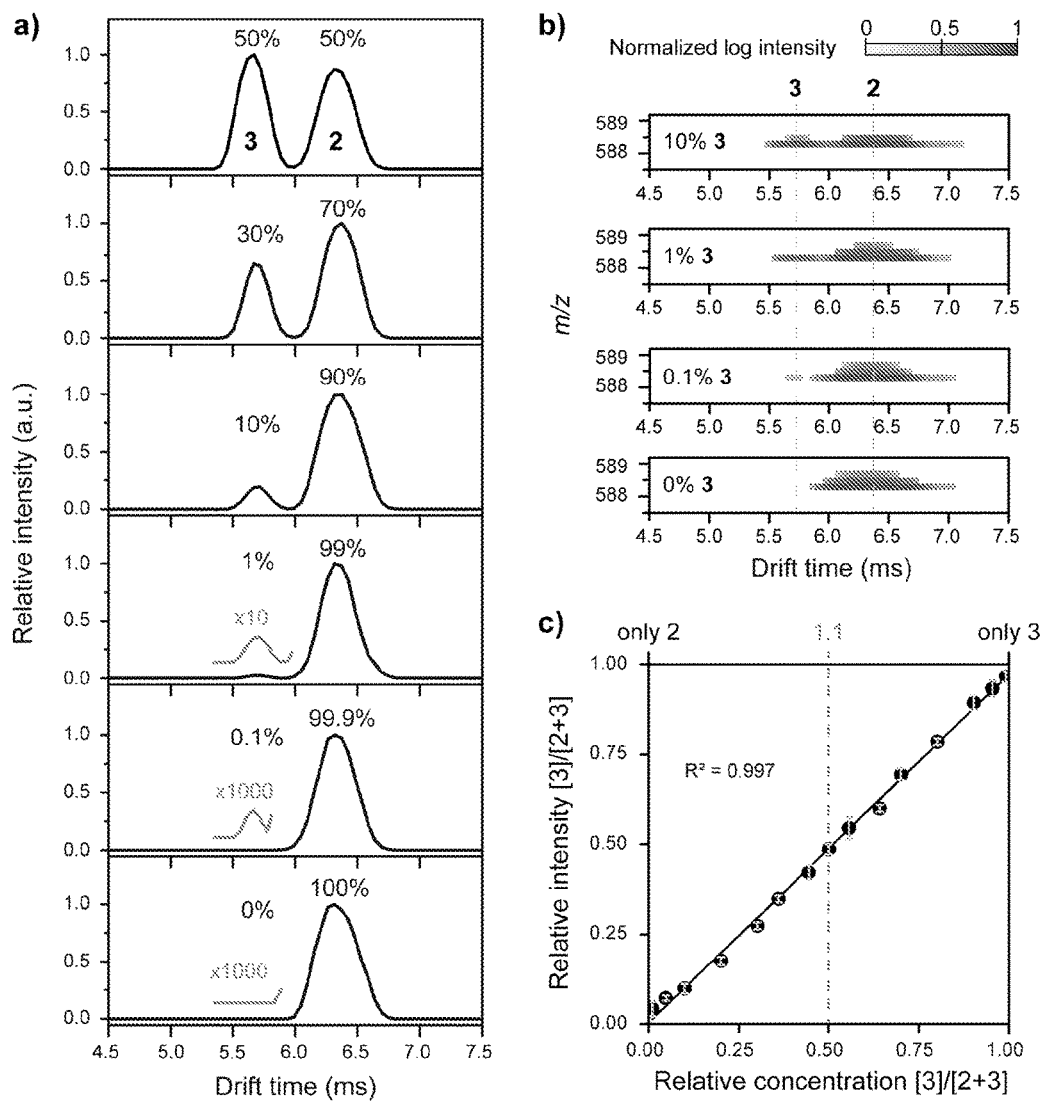
FIG. 8: Relative quantification of configurational trisaccharide isomers. Mixtures of the configurational isomers 2 and 3 were measured using IM-MS. a) The amount of 2 was kept constant while 3 was diluted to yield relative concentrations of 50%, 30%, 10%, 1%, 0.1%, and 0%. Minor components with relative concentrations as low as 0.1% can still be qualitatively detected. b) 3D plot showing the separation of anomers 2 and 3. The intensity is plotted using a logarithmic scale and impurities of 0.1% can be clearly identified without magnification. c) Plot of the relative concentration of 3 against the corresponding relative IM-MS intensity to illustrate the dynamic range of the method. A value of 0.5 represents equal amounts of 2 and 3, while 0 and 1 indicate the presence of only 2 or 3, respectively. The grey error bars correspond to the double standard deviation observed for three independent replicates.
Figure 9:
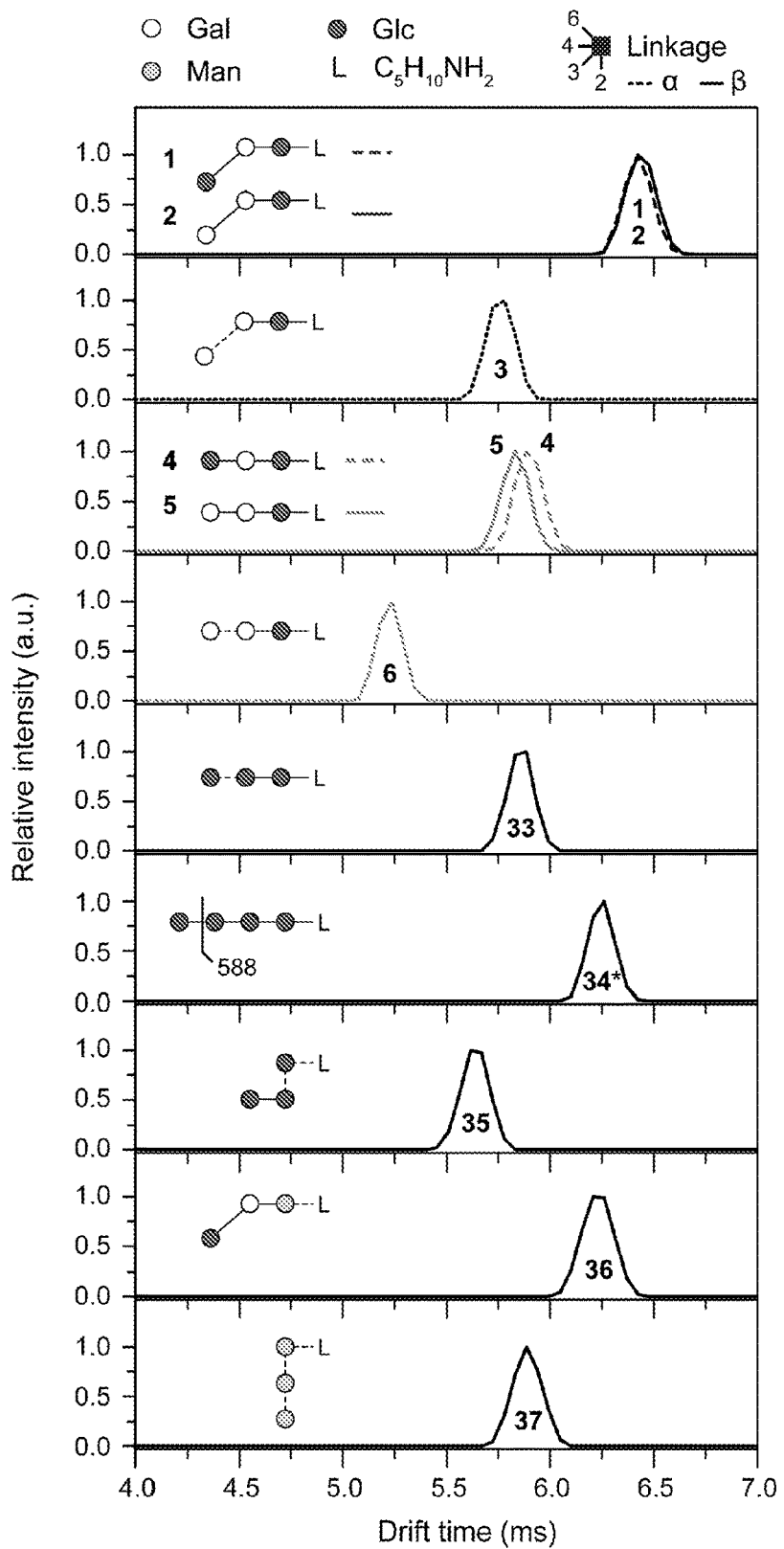
FIG. 9: Arrival time distributions of the deprotonated trisaccharides 1-6, 33, 35-37 and the isobaric fragment ion 34*. For the investigated $[M-H]^-=588$ trisaccharide ions large differences in drift time are observed. When isomer pairs that differed only in the configuration of the last glycosidic bond (2/3, 5/6, 33/34*) were compared, the α anomer showed a shorter drift time compared to the β anomer in all cases. Furthermore, carbohydrates that exhibit the same stereo- and regiochemistry of the glycosidic bonds, but a different composition of the building blocks (5/34*, 6/33) can be differentiated. Taken together this indicates that isomers, which differ in regio- or stereochemistry at one site typically exhibit drift time differences large enough to enable their differentiation.

Extraction of the ATD of the 588.4 m/z ion showed two separate arrival times, each of which corresponded to one of the two isomers. The area under the ATD is related to the concentration of the sample. Therefore, the theoretical concentration ratio x(3) was compared to the ratio of the drift time peak areas Int$_{rel}$(3)=A[3]/(A[2]+A[3]) (see FIG. 8). A linear correlation was observed, demonstrating the semiquantification of one isomer in the presence of another, down to contents of 1% of the minor component. Relative concentrations between 1 and 0.1% were still qualitatively detectable, but a determination of the relative content was not possible anymore due to detector saturation caused by the major component.

The invention claimed is:

1. A method for determining the structure of a target carbohydrate by ion mobility-mass spectrometry in negative ionization mode comprising the steps:
   A) providing a sample containing the target carbohydrate; and
   B) providing a database comprising the structures of the target carbohydrates and for each of the structures of the target carbohydrates the collision cross section value and the mass-to-charge ratio value of the negative ion thereof; and
   C) measuring the drift time value and the mass-to-charge ratio value of a negative ion of the target carbohydrate; and
   D) converting the drift time value measured at step C) to the corresponding collision cross section value; and
   E) comparing the collision cross section value determined at step D) and the mass-to-charge ratio value measured at step C) with the cross section values and mass-to-charge ratio values stored in the database; and
   F) determining the structure of the target carbohydrate, wherein determining the structure of the target carbohydrate comprises determining the stereochemistry of each of the anomeric carbons of the target carbohydrate.

2. The method according to claim 1, further comprising steps E1), E2), E3) and E4) performed after step E) and before step F):
- E1) subjecting a negative ion of the target carbohydrate to fragmentation to generate fragments of the negative ion of the target carbohydrate;
- E2) measuring the drift time values and the mass-to-charge ratio values of the fragments of the negative ion of the target carbohydrate, which were generated at step E1);
- E3) converting the drift time values measured at step E2) to the corresponding collision cross section values; and
- E4) comparing the collision cross section values determined at step E3) and the mass-to-charge ratio values measured at step E2) of the fragments of the negative ion of the target carbohydrate with cross section values and mass-to-charge ratio values stored in the database.

3. The method according to claim 2, further comprising step G) which is performed after step F):
- G) storing the structure of the target carbohydrate determined at step F) and the collision cross section value determined at step D) and mass-to-charge ratio value determined at step C) of the negative ion thereof in the database.

4. The method according to claim 2, wherein the fragmentation performed at step E1) results from collision induced dissociation (CID), electron-transfer dissociation (ETD) or electron-capture dissociation (ECD).

5. The method according to claim 1 or 2, wherein the database of step B) further comprises the structures of the fragments of the negative ions of the target carbohydrates and for each of the structures of the fragments of the negative ions of the target carbohydrates the collusion cross section value and the mass-to-charge ratio value of the fragment of the negative ion of the target carbohydrate.

6. The method according to claim 1, wherein determining the structure of a target carbohydrate comprises determining the compositional structure of the target carbohydrate.

7. The method according to claim 6, further comprising step G) which is performed after step F):
- G) storing the structure of the target carbohydrate determined at step F) and the collision cross section value determined at step D) and mass-to-charge ratio value determined at step C) of the negative ion thereof in the database.

8. The method according to claim 1, wherein the negative ion of the target carbohydrate is selected from the group comprising the deprotonated ion of the target carbohydrate and the anion complex of the target carbohydrate with chloride ($Cl^-$), acetate ($CH_3CO_2^-$), monochloroacetate ($CH_2ClCO_2^-$), dichloroacetate ($CHCl_2CO_2^-$), trichloroacetate ($CCl_3CO_2^-$), trifluoroacetate ($CF_3CO_2^-$), formate ($HCO_2^-$), monobromoacetate ($CH_2BrCO_2^-$), dibromoacetate ($CHBr_2CO_2^-$), tribromoacetate ($CBr_3CO_2^-$), bromochloroacetate ($CBrClHCO_2^-$), chlorodibromoacetate ($CClBr_2CO_2^-$), bromodichloroacetate ($CBrCl_2CO_2^-$), nitrate ($NO_3^-$) or phosphate ($H_2PO_4^-$).

9. The method according to claim 1, wherein the negative ion of the target carbohydrate is the deprotonated ion of the target carbohydrate.

10. The method according to claim 1, wherein the target carbohydrate is a synthetic carbohydrate or a carbohydrate isolated from natural sources.

11. The method according to claim 10, wherein the target carbohydrate is a synthetic carbohydrate and the synthetic carbohydrate further comprises a linker covalently bound to the anomeric carbon of the reducing end monosaccharide of the synthetic carbohydrate.

12. The method according to claim 1, wherein the target carbohydrate comprises between 1 and 50 monosaccharides.

13. The method according to claim 1, wherein the concentration of target carbohydrate in the sample provided at step A) is at least of 0.2 µg/m L.

14. The method according to claim 1, wherein the sample containing the target carbohydrate provided at step A) contains at least a further target carbohydrate, which is isobaric with the target carbohydrate.

15. The method according to claim 14, further comprising step H), which is performed after step F)
- H) determining the relative concentration ratio of each of the target isobaric carbohydrates in the sample.

* * * * *